(12) United States Patent
Sista et al.

(10) Patent No.: US 8,846,414 B2
(45) Date of Patent: Sep. 30, 2014

(54) DETECTION OF CARDIAC MARKERS ON A DROPLET ACTUATOR

(75) Inventors: Ramakrishna Sista, Morrisville, NC (US); Vamsee K. Pamula, Durham, NC (US); Arjun Sudarsan, San Diego, CA (US); Vijay Srinivasan, San Diego, CA (US); Michael G. Pollack, San Diego, CA (US); Richard B. Fair, Durham, NC (US); Allen E. Eckhardt, San Diego, CA (US)

(73) Assignees: Advanced Liquid Logic, Inc., Research Triangle Park, NC (US); Duke University, Durham, NC (US)

( * ) Notice: Subject to any disclaimer, the term of this patent is extended or adjusted under 35 U.S.C. 154(b) by 669 days.

(21) Appl. No.: 12/569,725

(22) Filed: Sep. 29, 2009

(65) Prior Publication Data

US 2011/0076692 A1    Mar. 31, 2011

Related U.S. Application Data

(63) Continuation-in-part of application No. 11/639,531, filed on Dec. 15, 2006, which is a continuation-in-part
(Continued)

(51) Int. Cl.
*G01N 33/553* (2006.01)
*G01N 33/68* (2006.01)
*G01N 33/543* (2006.01)

(52) U.S. Cl.
CPC ........ *G01N 33/6893* (2013.01); *G01N 2800/32* (2013.01); *G01N 2333/4712* (2013.01); *G01N 2333/58* (2013.01); *G01N 33/54366* (2013.01)
USPC ........... 436/518; 436/536; 436/525; 436/174; 435/283.1; 435/287.1; 435/287.2; 435/287.3

(58) Field of Classification Search
USPC ............... 436/518, 525, 174, 536; 435/283.1, 435/287.1, 287.2, 287.3
See application file for complete search history.

(56) References Cited

U.S. PATENT DOCUMENTS

| 4,636,785 A | 1/1987 | Le Pesant |
| 5,181,016 A | 1/1993 | Lee |

(Continued)

FOREIGN PATENT DOCUMENTS

| WO | 0069565 A1 | 11/2000 |
| WO | 0073655 A1 | 12/2000 |

(Continued)

OTHER PUBLICATIONS

Chakrabarty et al., "Design Automation Challenges for Microfluidics-Based Biochips", DTIP of MEMS & MOEMS, Montreux, Switzerland, Jun. 1-3, 2005.
(Continued)

*Primary Examiner* — Melanie Y Brown
(74) *Attorney, Agent, or Firm* — William A. Barrett; Ward & Smith, P.A.

(57) ABSTRACT

The present invention provides for the detection of cardiac markers on a droplet actuator. An aspect provides a method of assaying a cardiac marker in a biological sample from a subject, the method including providing a droplet actuator, loading the biological sample and assay reagents on the droplet actuator, executing droplet operations to create sample droplets from the sample and reagent droplets from the reagents on the droplet actuator, and executing droplet operations using the sample droplets and reagent droplets to produce a detectable signal indicative of the quantity of the cardiac marker in the biological sample. Still other aspects are provided.

55 Claims, 11 Drawing Sheets

Related U.S. Application Data of application No. PCT/US2006/047486, filed on Nov. 12, 2006.

(60) Provisional application No. 61/103,302, filed on Oct. 7, 2008, provisional application No. 61/122,791, filed on Dec. 16, 2008, provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006.

(56) References Cited

U.S. PATENT DOCUMENTS

| | | |
|---|---|---|
| 5,486,337 A | 1/1996 | Ohkawa |
| 5,604,105 A * | 2/1997 | Jackowski ............... 435/7.4 |
| 6,130,098 A | 10/2000 | Handique et al. |
| 6,294,063 B1 | 9/2001 | Becker et al. |
| 6,565,727 B1 | 5/2003 | Shenderov |
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,763,471 B2 | 7/2010 | Pamula et al. |
| 7,767,435 B2 * | 8/2010 | Chiu et al. ............... 435/286.5 |
| 7,815,871 B2 | 10/2010 | Pamula et al. |
| 7,816,121 B2 | 10/2010 | Pollack et al. |
| 7,851,184 B2 | 12/2010 | Pollack et al. |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,048,628 B2 | 11/2011 | Pollack et al. |
| 2002/0005354 A1 | 1/2002 | Spence et al. |
| 2002/0031446 A1 * | 3/2002 | Friedlander et al. ......... 422/68.1 |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055891 A1 * | 3/2004 | Pamula et al. ............... 205/98 |
| 2004/0058450 A1 | 3/2004 | Pamula et al. |
| 2004/0231987 A1 | 11/2004 | Sterling et al. |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 * | 10/2007 | Pamula et al. ............... 210/806 |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0302431 A1 | 12/2008 | Marchand et al. |
| 2009/0014394 A1 | 1/2009 | Yi et al. |
| 2009/0042319 A1 | 2/2009 | De Guzman et al. |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0291433 A1 | 11/2009 | Pollack et al. |
| 2010/0025242 A1 | 2/2010 | Pamula et al. |

FOREIGN PATENT DOCUMENTS

| | | |
|---|---|---|
| WO | 2004029585 A1 | 4/2004 |
| WO | 2004030820 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006138543 | 12/2006 |
| WO | 2007048111 | 4/2007 |
| WO | 2007120240 A2 | 10/2007 |
| WO | 2007120241 A2 | 10/2007 |
| WO | 2007123908 A2 | 11/2007 |

OTHER PUBLICATIONS

Chakrabarty et al., "Design Automation for Microfluidics-Based Biochips", ACM Journal on Engineering Technologies in Computing Systems, 1(3), Oct. 2005, 186-223.

Chakrabarty, "Design, Testing, and Applications of Digital Microfluidics-Based Biochips", Proceedings of the 18th International Conf. On VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

(56) References Cited

OTHER PUBLICATIONS

Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro- Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99/3800, 30th AIAA Fluid Dynamics Conference, Norfolk, VA, (Invited lecture), Jun. 1999, pp. 1-6.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (Therminic), 2005, 278-83.
Paik et al., "Electrowetting-based droplet mixers for microfluidic systems", Lab on a Chip (LOC), vol. 3.(more mixing videos available, along with the article, at LOC's website), 2003, 28-33.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006,1-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pollack et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High—Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Intl Conference on Micro Total Analysis Systems (mTAS), Squaw Valley, CA, Oct. 5-9, 2003, 619-622.
Ren et al., "Automated electrowetting-based droplet dispensing with good reproducibility", Proc. Micro Total Analysis Systems (mTAS), 7th Int. Conf. on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowettingbased droplet-on-chip chemical dilution", Transducers, 12th International Conference on Solid—State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro. Electro Mechanical Systems Workshop, Heidelberg, Germany, Jan. 1998, pp. 454-459.
Srinivasan et al., "3-D imaging of moving droplets for microfluidics using optical coherence tomography", Proc. 7th International Conference on Micro Total Analysis Systems (mTAS), Squaw Valley, CA, Oct 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.

(56) References Cited

OTHER PUBLICATIONS

Srinivasan, "A Digital Microfluidic Lab-on-a-Chip for Clinical Diagnostic Applications", Ph.D. thesis, Dept of Electrical and Computer Engineering, Duke University, 2005.

Srinivasan et al., "An integrated digital microfluidic lab-on-a-chip for clinical diagnostics on human physiological fluids", Lab on a Chip, vol. 4, 2004, 310-315.

Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct 5-9, 2003, 1287-1290.

Srinivasan et al., "Droplet-based microfluidic lab-on-a-chip for glucose detection", Analytica Chimica Acta, vol. 507, No. 1, 2004, 145-150.

Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 72-75.

Su et al., "Yield Enhancement of Digital Microfluidics-Based Biochips Using Space Redundancy and Local Reconfiguration", Proc. Design, Automation and Test in Europe (Date) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published online, May 2004, 3229-3235.

Wang et al., "Droplet-based micro oscillating-flow PCR chip", J. Micromechanics and Microengineering, vol. 15, 2005, 1369-1377.

Xu et al., "Droplet-Trace-Based Array Partitioning and a Pin Assignment Algorithm for the Automated Design of Digital Microfluidic Biochips", Codes, 2006, 112-117.

Yao et al., "Spot Cooling Using Thermoelectric Microcooler", Proc. 18th Int. Thermoelectric Conf, Baltimore, VA, pp. 256-259, Aug. 1999.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

\* cited by examiner

DETECTION OF CARDIAC MARKERS ON A DROPLET ACTUATOR

RELATED APPLICATIONS

This patent application is a continuation-in-part of U.S. patent application Ser. No. 11/639,531, entitled "Droplet-Based Washing," filed Dec. 15, 2006 and is a continuation-in-part of International Patent Application No. PCT/US2006/47486, entitled "Droplet-Based Biochemistry," filed Dec. 11, 2006, both of which claim priority to U.S. Patent Application Nos. 60/745,058, entitled "Filler Fluids for Droplet-Based Microfluidics" filed on April 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006.

This patent application also relates to, claims priority to, and incorporates by reference the entire disclosures of U.S. Patent Application Nos. 61/103,302, entitled "Bead Incubation and Washing on a Droplet Actuator," filed on Oct. 7, 2008 and 61/122,791, entitled "Bead Incubation and Washing on a Droplet Actuator," filed on Dec. 16, 2008.

GOVERNMENT INTEREST

This invention was made with government support under CA114993, awarded by the National Cancer Institute of the National Institutes of Health. The United States Government has certain rights in the invention.

BACKGROUND

A droplet actuator typically includes one or more substrates configured to form a surface or gap for conducting droplet operations. The one or more substrates include electrodes and establish a droplet operations surface or gap for conducting droplet operations. The droplet operations substrate or the gap between the substrates may be coated or filled with a filler fluid that is immiscible with the liquid that forms the droplets. Droplet operations are controlled by the electrodes. In related work, the inventors have used droplet actuators in a variety of applications, including immunoassays (e.g., enzyme linked immunosorbent assays (ELISA)) Immunoassays are among the most sensitive and specific analytical methods that are routinely used in clinical laboratories.

Cardiac markers are commonly measured to evaluate health. For example, cardiac markers may be measured to evaluate heart function or assess heart disease. Among other things, cardiac markers may be measured to assess acute coronary syndromes, identify and manage patients at risk of acute myocardial infarction (AMI), triage patients with chest pain, and/or assess reperfusion status following thrombolytic therapy. Examples of cardiac markers include aspartate transaminase (AST); atrial natriuretic peptide (ANP); brain natriuretic peptide (BNP); brain natriuretic propeptide (proBNP); cardiac troponin (cTn); cardiac troponin complex subunits I, C and T (cTnI, cTnC, cTnT); cardiac cTnIsoforms; C-reactive protein (CRP); creatine kinase-MB (CKMB); C-type natriuretic peptide (CNP); cystatin C (CSC); fatty acid binding protein (FABP); glycogen phosphate isoenzyme BB (GPBB); ischemia-modified albumin (IMA); lactate dehydrogenase (LDH); myeloperoxidase (MPO); Mb (Mb); N-terminal fragment of brain natriuretic propeptide (NT-proBNP); placental growth factor (PIGF); pregnancy-associated plasma protein-A (PAPPA); sCD40 ligand; and various fragments and isoforms of the foregoing.

Measurements of cardiac markers provide a highly effective means of evaluating chest pain, but results of the test are often not available on an immediate-need basis. There is a need for improved methods of multiplexing immunoassays for detection of cardiac markers that provides for small sample size, flexibility in cardiac marker panel design, and real-time diagnosis of these markers.

BRIEF DESCRIPTION OF THE INVENTION

The present invention is directed to the detection of cardiac markers on a droplet actuator.

In one embodiment, a method of assaying a cardiac marker in a biological sample from a subject is provided, the method comprising providing a droplet actuator, loading the biological sample and assay reagents on the droplet actuator, executing droplet operations to create sample droplets from the sample and reagent droplets from the reagents on the droplet actuator, and executing droplet operations using the sample droplets and reagent droplets to produce a detectable signal indicative of the quantity of the cardiac marker in the biological sample.

DEFINITIONS

As used herein, the following terms have the meanings indicated:

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Corp., Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication No. 20050260686, entitled, "Multiplex flow assays preferably with magnetic particles as solid phase," published on Nov. 24, 2005, the entire disclosure of which is incorporated herein by reference for its teaching concerning magnetically responsive materials and beads. Beads may be pre-coupled with a biomolecule (ligand). The ligand may, for example, be an antibody, protein or antigen, DNA/RNA probe or any other molecule with an affinity for the desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling fluid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. The terms "merge-and-split" and "split-and-merge" are used interchangeably to refer to droplet operations sequences in which involve various combinations of merging and splitting in any order. For example, the operations may be merge-split-merge-split, split-merge-split-merge, merge-split-merge-merge-split, merge-split-split-merge-split-split, and generally any combination of merging and splitting which achieves the stated objective, such as effective circulation of beads during incubation or effective washing of beads in a merge-and-split wash protocol.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DESCRIPTION

Figure 1A:
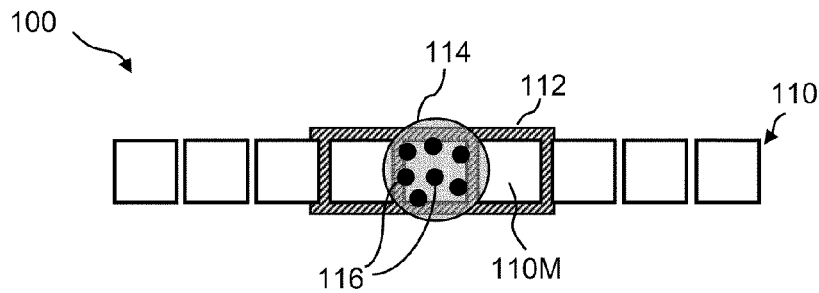
FIGS. 1A, 1B, 1C, 1D, and 1E illustrate top views of a portion of a droplet actuator and show a process of performing droplet operations to improve the dynamic range of signal detection.

The invention provides a droplet actuator device and methods of using the device for detection of cardiac markers. The methods include, among other things, droplet-based immunoassays for measuring cardiac markers. The invention also includes methods for conducting multiplexed immunoassays for measuring cardiac markers. The multiplexed immunoassays may be used to detect different cardiac markers on a single droplet actuator and/or detect the same cardiac markers using samples from different subjects and/or multiple samples from the same subject on a single droplet actuator.

The devices and methods of the invention are also generalizable to the field of immunoassays, and are not restricted to the measurement of cardiac markers. Thus, the invention also includes methods for conducting multiplexed immunoassays for measuring analytes other than cardiac markers. The multiplexed immunoassays may be used to detect different analytes on a single droplet actuator and/or detect the same analytes using samples from different subjects and/or multiple samples from the same subject on a single droplet actuator.

7.1 Sample and Analytes

While the focus of this specification is on the measurement of cardiac markers, it will be appreciated that the devices and methods of the invention may be used with any desired set of analytes. The invention is useful for detecting any set of analytes detectable by affinity assay, such as an immunoassay. Examples include analytes that useful in diagnosis, prognosis, risk assessment, treatment monitoring, and/or provision of appropriate treatment. The analytes may, for example, include analytes from natural or non-natural sample sources. Examples include analytes from biological samples, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, single cells, multicellular analytes, organelles, fluidized tissues, fluidized organisms, multicellular organisms, biological swabs and biological washes.

With respect to cardiac markers, the invention is useful for detecting any set of cardiac markers detectable by affinity assay, such as an immunoassay. Examples include analytes that useful in diagnosis, prognosis, risk assessment, treatment monitoring, and/or provision of appropriate treatment for heart conditions, such as chronic or acute heart conditions. For example, analytes may be selected for their utility in assessing AMI; identifying subjects at risk of AMI; and/or managing subjects at risk of AMI. In another example, analytes may be selected for their utility in triaging patients with chest pain. And in yet another example, analytes may be selected for their utility in assessing reperfusion status following thrombolytic therapy.

In some cases, the analytes may include one or more biological markers (biomarkers). The biomarkers may, for example, be selected for evaluation as indicators of normal biological processes, pathogenic processes, or pharmacological responses to a therapeutic intervention. Examples of biomarkers include Type 0 biomarkers, which are markers of the natural history of a disease and correlate longitudinally with known clinical indices; Type I biomarkers, which are markers of effects of a therapeutic intervention in accordance with its mechanism of action; and surrogate end points (aka Type 2 biomarkers), which are markers that substitute for a clinical end point and are expected to predict clinical benefit, harm, or lack of benefit or harm, on the basis of epidemiological, therapeutic, pathophysiological, or other scientific evidence. In some cases, the analytes may include one or more risk factor markers, which are associated with a disease because they are in the causal pathway leading to the disease. In some cases, the analytes may include one or more risk markers associated with the disease (statistically) but not necessarily causally linked (e.g., factors which are measures of a disease process). For additional details concerning the selection of biomarkers of cardiovascular disease, see R. Vasan, "Biomarkers of Cardiovascular Disease Molecular Basis and Practical Considerations," *Circulation* 113:2335-2362 (2006), the entire disclosure of which is incorporated herein by reference.

Specific, nonlimiting examples of cardiac markers include: AST, ANP, BNP, proBNP, NT-proBNP, cTn, cTnI, cTnC, cTnT, cTn isoforms, CRP, CKMB, CNP, CSC, FABP, GPBB, IMA, LDH, MPO, Mb, PIGF, PAPPA, and sCD40 ligand.

In addition, it should be noted that, as discussed in Section 7.3, a droplet actuator of the invention and associated methods may be employed to assess analytes other than analytes that are suitable for affinity-type assays. Thus, for example, in addition to conducting immunoassays for cardiac markers or other analytes, a droplet actuator of the invention may conduct one or more other assay types, such as assays for enzyme activity or assays involving PCR and/or nucleic acid sequencing, such as SNP detection or detection of infectious agents by nucleic acid sequencing. As another example, the invention provides, on a single droplet actuator: (a) detection of immunoassays for 2, 3, 4, 5, or more cardiac markers, along with (b) one or more assays involving amplification of the subject's DNA or other nucleic acids and detection of 1, 2, 3, 4, 5 or more nucleotide sequences associated with a heart condition; and/or (c) one or more assays involving amplification of nucleic acids amplification of non-host DNA or other nucleic acids and detection of 1, 2, 3, 4, 5 or more nucleotide sequences associated with infectious agents, such as bacteria, viruses, or parasites associated with a heart condition. Furthermore, these multiplexed analyses may be performed using sample from one or more subjects on a single droplet actuator. Thus, the analysis may be multiplexed with respect to assay types, multiplexed with respect to samples, and/or multiplexed with respect to subjects.

The droplet actuator device and assay methods of the invention make use of a small sample volume. For example, a suitable sample volume is in the range of from about 0.001 µL to about 100 µL, preferably from about 0.01 µL to about 50 µL, more preferably from about 0.1 µL to about 25 µL, and still more preferably from about 1 µL to about 20 µL. The sample volume may be dispensed using droplet operations into yet smaller volumes for use in conducting assays.

Samples are provided from a subject in need of testing, such as a subject for whom measurement of cardiac markers is useful for diagnosis, prognosis, risk assessment, treatment monitoring, and/or provision of appropriate treatment. In some cases, samples are provided from subjects who are known or suspected to have experienced myocardial injury. Samples selected for cardiac marker testing according to the invention are samples that include or may include one or more cardiac markers. As a non-limiting example, samples may include biological fluids or other fluids which include cardiac markers such as those described herein. With regard to cardiac markers and other analytes, examples of suitable sample substances or components include: whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, tissue samples, liquids containing multi-celled organisms, biological swabs and biological washes. Sample liquids may also include other non-sample components, such as reagents. Examples of reagents include water, deionized water, saline solutions, acidic solutions, basic solutions, detergent solutions and/or buffers. As an example, the sample liquid may include a reagent for a biochemical protocol, such as a nucleic acid amplification protocol, an affinity-based assay protocol, an enzymatic assay protocol, a sequencing protocol, and/or a protocol for analyses of biological fluids.

7.2 Rapid Analyte Measurement

The droplet actuator device and assay methods of the invention provide for rapid detection of analytes. In certain non-limiting examples, less than about 10 minutes elapses from the time a sample is loaded onto the droplet actuator until the time that a measurement is taken and/or a result is displayed; or less than about 9 minutes elapses from the time a sample is loaded onto the droplet actuator until the time that a measurement is taken and/or a result is displayed; or less than about 8 minutes elapses from the time a sample is loaded onto the droplet actuator until the time that a measurement is taken and/or a result is displayed; or less than about 7 minutes elapses from the time a sample is loaded onto the droplet actuator until the time that a measurement is taken and/or a result is displayed; or less than about 6 minutes elapses from the time a sample is loaded onto the droplet actuator until the time that a measurement is taken and/or a result is displayed; or less than about 5 minutes elapses from the time a sample is loaded onto the droplet actuator until the time that a measurement is taken and/or a result is displayed; or less than about 4 minutes elapses from the time a sample is loaded onto the droplet actuator until the time that a measurement is taken and/or a result is displayed; or less than about 3 minutes elapses from the time a sample is loaded onto the droplet actuator until the time that a measurement is taken and/or a result is displayed; or less than about 2 minutes elapses from the time a sample is loaded onto the droplet actuator until the time that a measurement is taken and/or a result is displayed; or less than about 1 minute elapses from the time a sample is loaded onto the droplet actuator until the time that a measurement is taken and/or a result is displayed.

In another example, less than about 10 minutes elapses from the time a sample is loaded onto the droplet actuator until the time that a measurement is taken and/or a result is displayed for 2 or more cardiac markers. In another example, less than about 10 minutes elapses from the time a sample is loaded onto the droplet actuator until the time that a measurement is taken and/or a result is displayed for 3 or more cardiac markers. In another example, less than about 10 minutes elapses from the time a sample is loaded onto the droplet actuator until the time that a measurement is taken and/or a result is displayed for 4 or more cardiac markers. In another example, less than about 10 minutes elapses from the time a sample is loaded onto the droplet actuator until the time that a measurement is taken and/or a result is displayed for 5 or more cardiac markers.

In another example, less than about 5 minutes elapses from the time a sample is loaded onto the droplet actuator until the time that a measurement is taken and/or a result is displayed for 2 or more cardiac markers. In another example, less than about 5 minutes elapses from the time a sample is loaded onto the droplet actuator until the time that a measurement is taken and/or a result is displayed for 3 or more cardiac markers. In another example, less than about 5 minutes elapses from the time a sample is loaded onto the droplet actuator until the time that a measurement is taken and/or a result is displayed for 4 or more cardiac markers. In another example, less than about 5 minutes elapses from the time a sample is loaded onto the droplet actuator until the time that a measurement is taken and/or a result is displayed for 5 or more cardiac markers.

In another example, less than about 600 seconds elapses from the time a sample is loaded onto the droplet actuator until the time that a measurement is taken and/or a result is displayed, and duration of incubation of the sample with analyte capture beads ranges from about 30 seconds to about 300 seconds. In another example, less than about 600 seconds elapses from the time a sample is loaded onto the droplet actuator until the time that a measurement is taken and/or a result is displayed, and duration of incubation of the sample with analyte capture beads ranges from about 60 to about 240 seconds. In another example, less than about 600 seconds elapses from the time a sample is loaded onto the droplet actuator until the time that a measurement is taken and/or a result is displayed, and duration of incubation of the sample with analyte capture beads is less than about 240 seconds. In another example, less than about 300 seconds elapses from the time a sample is loaded onto the droplet actuator until the time that a measurement is taken and/or a result is displayed, and duration of incubation of the sample with analyte capture beads ranges from about 30 seconds to about 180 seconds. In another example, less than about 300 seconds elapses from the time a sample is loaded onto the droplet actuator until the time that a measurement is taken and/or a result is displayed, and duration of incubation of the sample with analyte capture beads ranges from about 60 to about 150 seconds. In another example, less than about 300 seconds elapses from the time a sample is loaded onto the droplet actuator until the time that a measurement is taken and/or a result is displayed, and duration of incubation of the sample with analyte capture beads is less than about 120 seconds. In another example, less than about 240 seconds elapses from the time a sample is loaded onto the droplet actuator until the time that a measurement is taken and/or a result is displayed, and duration of incubation of the sample with analyte capture beads is less than about 120 seconds. The duration of incubation is the time from the first introduction of sample to the beads to the first introduction of a wash droplet to the bead-containing droplet.

In another example, less than about 600 seconds elapses from the time a sample is loaded onto the droplet actuator until the time that a measurement is taken and/or a result is displayed, and duration of washing of the analyte capture beads ranges from about 30 seconds to about 360 seconds. In another example, less than about 600 seconds elapses from the time a sample is loaded onto the droplet actuator until the time that a measurement is taken and/or a result is displayed, and duration of washing of the analyte capture beads ranges from about 60 to about 300 seconds. In another example, less than about 600 seconds elapses from the time a sample is loaded onto the droplet actuator until the time that a measurement is taken and/or a result is displayed, and duration of washing of the analyte capture beads is less than about 300 seconds. In another example, less than about 300 seconds elapses from the time a sample is loaded onto the droplet actuator until the time that a measurement is taken and/or a result is displayed, and duration of washing of the analyte capture beads ranges from about 30 seconds to about 240 seconds. In another example, less than about 300 seconds elapses from the time a sample is loaded onto the droplet actuator until the time that a measurement is taken and/or a result is displayed, and duration of washing of the analyte capture beads ranges from about 60 to about 180 seconds. In another example, less than about 300 seconds elapses from the time a sample is loaded onto the droplet actuator until the time that a measurement is taken and/or a result is displayed, and duration of washing of the analyte capture beads is less than about 180 seconds. In another example, less than about 240 seconds elapses from the time a sample is loaded onto the droplet actuator until the time that a measurement is taken and/or a result is displayed, and duration of washing of the analyte capture beads is less than about 180 seconds. The duration of washing is the time from the first introduction of the wash buffer to the beads for the washing protocol to the last splitting off of a supernatant droplet from the bead-containing droplet.

In another example, less than about 600 seconds elapses from the time a sample is loaded onto the droplet actuator until the time that a measurement is taken and/or a result is displayed, and duration of detection ranges from about 30 seconds to about 180 seconds. In another example, less than about 600 seconds elapses from the time a sample is loaded onto the droplet actuator until the time that a measurement is taken and/or a result is displayed, and duration of detection ranges from about 60 to about 150 seconds. In another example, less than about 600 seconds elapses from the time a sample is loaded onto the droplet actuator until the time that a measurement is taken and/or a result is displayed, and duration of detection is less than about 150 seconds. In another example, less than about 300 seconds elapses from the time a sample is loaded onto the droplet actuator until the time that a measurement is taken and/or a result is displayed, and duration of detection ranges from about 30 seconds to about 180 seconds. In another example, less than about 300 seconds elapses from the time a sample is loaded onto the droplet actuator until the time that a measurement is taken and/or a result is displayed, and duration of detection ranges from about 60 to about 180 seconds. In another example, less than about 300 seconds elapses from the time a sample is loaded onto the droplet actuator until the time that a measurement is taken and/or a result is displayed, and duration of detection is less than about 180 seconds. In another example, less than about 240 seconds elapses from the time a sample is loaded onto the droplet actuator until the time that a measurement is taken and/or a result is displayed, and duration of detection is less than about 180 seconds. The duration of detection is the time from the first production of the signal that is measured for detection purposes until detection is stopped or until the droplet is transported using droplet operations away from the detection zone.

7.3 Multiplexing

The invention provides, among other things, a multiplexed immunoassay process in which two or more different analytes are tested on a single droplet actuator. A sample may be loaded on the droplet actuator, divided into subsamples using droplet operations, and a droplet-based immunoassay protocol may be executed on each of the subsamples. This type of multiplexing is a type of spatial multiplexing, and involves different analytical reactions in different droplets. In another embodiment, a sample may be loaded on the droplet actuator, and a droplet-based immunoassay protocol may be executed on the sample or on a subsample thereof, where multiplexing is achieved within a droplet, e.g., using chemically or physically differentiable beads or signaling molecules. This type of multiplexing may involve spatial multiplexing in which location of beads are determined within a droplet and/or signal multiplexing in which differentiable signals from a droplet are analyzed to identify and/or quantify different analytes within a droplet without requiring a determination of location. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005; the entire disclosures of which are incorporated herein by reference.

In various embodiments, multiplexing may include spatial and/or signal multiplexing. In one embodiment, using spatial multiplexing, several different immunoassays may be performed simultaneously in independent droplets. For example, n different immunoassays may be performed on a common droplet operations surface in separate, individual droplets from a single parent sample liquid, where n=2, 3, 4, 5, 6, 7, 8, 9, 10 or more.

As an example, the invention provides a multiplexed analysis of one or more cardiac markers. The cardiac markers may, in a nonlimiting example, include all or a subset of the following: AST, ANP, BNP, proBNP, NT-proBNP, cTn, cTnI, cTnC, cTnT, cTn isoforms, CRP, CKMB, CNP, CSC, FABP, GPBB, IMA, LDH, MPO, Mb, PIGF, PAPPA, and/or sCD40 ligand. The multiplexed analysis may include spatial and/or signal multiplexing of two or more cardiac markers. Further, the multiplexed analysis may include spatial and/or signal multiplexing of two or more cardiac markers selected from AST, ANP, BNP, proBNP, NT-proBNP, cTn, cTnI, cTnC, cTnT, cTn isoforms, CRP, CKMB, CNP, CSC, FABP, GPBB, IMA, LDH, MPO, Mb, PIGF, PAPPA, and sCD40 ligand. In any of the multiplexed panels, other cardiac markers may also be included. In any of the multiplexed panels, other diagnostic analytes may also be included.

In one embodiment, the invention provides methods for characterizing cardiac markers or other analytes, wherein the methods include exposing a sample of biological fluid from a patient to a pooled population of particles, wherein a first subset of particles is bound to a reactant that binds an antibody and a second subset of particles is bound to a reactant that binds an antigen. The methods further include conducting a bead washing operation on a droplet actuator to remove unbound material, measuring signal from the washed beads, and determining based on the signal a ratio of measured amounts of the antibody and the antigen in the sample. In some cases, the ratio is compared to one or more standard ratios. In other embodiments, the steps of exposing and determining a ratio of antibody to antigen are repeated for one or more additional samples of biological fluid taken from the patient, and at least two ratios are compared to analyze a progression of the disease. Further explanation of this method and its application to characterizing immune disorders is set forth in U.S. Patent Publication No. 20090068680, entitled "Method for Characterizing Immune Disorders."

7.4 Sample Pre-Concentration

For analyses requiring detection of very low concentrations of cardiac markers, droplet pre-concentration techniques may be used to improve the limits of detection. As an example, droplet pre-concentration may be accomplished by exposing beads having affinity for the desired analytes to several droplets, then combining the beads into a lesser number of droplets or a single droplet. Combining beads from multiple droplets may, for example, be performed by merging two or more bead containing droplets to yield a combined droplet including beads from the two or more droplets; restraining the beads using a physical barrier and/or a magnetic field; and splitting the droplet to yield a first droplet with a more concentrated set of beads and a second droplet, which is a supernatant droplet that includes few beads or substantially no beads. Another example of droplet pre-concentration involves serially incubating multiple sample droplets with a single set of beads. The serial incubation approach may, for example, involve: combining (e.g., using droplet operations) a bead-containing droplet with a first sample droplet; immobilizing the beads and using a droplet splitting operation to split off a supernatant droplet that includes few beads or substantially no beads; combining the bead-containing droplet with a second sample droplet; repeating the droplet splitting process. In this manner, 2, 3, 4, 5, 6, 7, 8, 9, 10 or more sample droplets may be serially exposed to a set of beads, thereby increasing the amount of analyte that is captured by the beads.

Sample pre-concentration may be conducted with multiple bead types, each type having affinity for a specific analyte or a specific set of analytes. Multiple bead types may be incubated with a single sample which has been divided into multiple droplets. In some cases, the bead types may be differentiable based on a characteristic of the beads, such as the bead characteristics described in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 200; the entire disclosures of which are incorporated herein by reference.

As one example, a sample is merged into sample droplets; each sample droplet is merged with a bead-containing droplet having a single bead type; the beads are immobilized and the combined droplet is split using droplet operations to yield a supernatant droplet and a bead-containing droplet. The process may be repeated using a series of sample droplets in order to increase the quantity of analyte captured on each bead. As another example, concentration of analyte on multiple bead types may be performed by merging two or more bead containing droplets, each droplet having multiple bead types, to provide a combined droplet comprising beads from the two or more droplets; restraining the beads using a physical barrier and/or a magnetic field; and splitting the droplet to yield a first droplet with a more concentrated set of beads having multiple bead types and a second droplet, which is a supernatant droplet. In yet another example, concentration of analyte on multiple bead types may be performed by merging two or more bead containing droplets, each droplet having a single bead type, to provide a combined droplet comprising beads from the two or more droplets; restraining the beads using a physical barrier and/or a magnetic field; and splitting the droplet to yield a first droplet with a more concentrated set of beads having multiple bead types and a second droplet, which is a supernatant droplet.

Thus, in some embodiments, prior to loading a sample onto a droplet actuator, analytes of interest are bound to capture beads. The beads may be concentrated into a small part of the processed sample volume. This portion of the sample volume that includes the capture beads is loaded onto the droplet actuator. The ratio of sample volume to loaded volume may, in some embodiments, range from about 2:1 to about 100:1; or from about 5:1 to about 100:1; or from about 5:1 to about 50:1; or from about 5:1 to about 25:1.

FIGS. 1A, 1B, 1C, 1D, and 1E illustrate top views of an electrode arrangement 100 and show a process of performing droplet operations to improve the dynamic range of signal detection. The dynamic range on the digital microfluidic platform may be programmed to account for samples that fall on either side of a standard curve. Since the signal output in an immunoassay (e.g., ELISA) is proportional to the amount of analyte captured, the sensitivity may be increased by increasing the number of sample droplets that are incubated with the magnetically responsive beads. Samples that are recovered above the top-end of the standard curve may be subjected to an auto-dilution sequence in order to bring the concentration of analytes back within range of detection and be accurately measured.

A droplet actuator may include droplet operations electrodes 110 (e.g., electrowetting electrodes) arranged for conducting droplet operations on a droplet operations surface, such as in a droplet operations gap of a droplet actuator. Magnet 112 is arranged in proximity to droplet operations electrodes 110. Magnet 112 is arranged such that certain droplet operations electrodes 110 (e.g., 3 droplet operations electrodes 110M) are sufficiently within the magnetic field of magnet 112 to immobilize or restrain beads 116 when a droplet is atop electrode 110M. Magnet 112 may, for example, be a permanent magnet or an electromagnet.

An example of a process of performing droplet operations to improve the dynamic range of signal detection may include, but is not limited to, some or all of the following steps, which may be electrode mediated using droplet operations on a droplet operations surface, such as within a droplet operations gap:

FIG. 1A shows a reagent droplet 114 including a quantity of magnetically responsive beads 116. Magnetically responsive beads 116 may have primary capture antibodies thereon. Reagent droplet 114 is positioned at a certain droplet operations electrode 110M within the magnetic field of magnet 112, such that magnetically responsive beads 116 are substantially restrained in their movement within droplet 114. Reagent droplet 114 may also include blocking proteins and secondary reporter antibodies, and these may be included in sample droplet 118 as well.

Figure 1B:
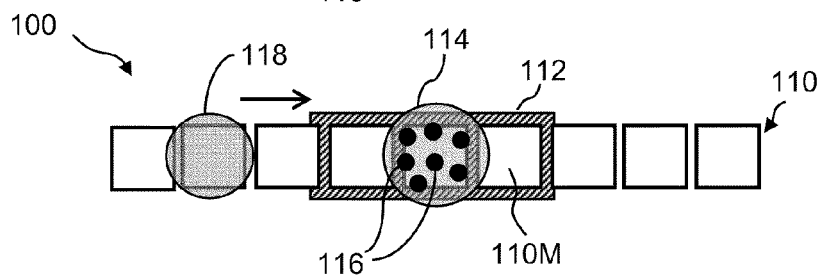

FIG. 1B shows sample droplet 118 merged with reagent droplet 114 using droplet operations to form a reaction droplet 120. In one example, sample droplet 118 may contain an analyte (e.g., a cardiac marker) to be evaluated in an immunoassay.

Figure 1C:
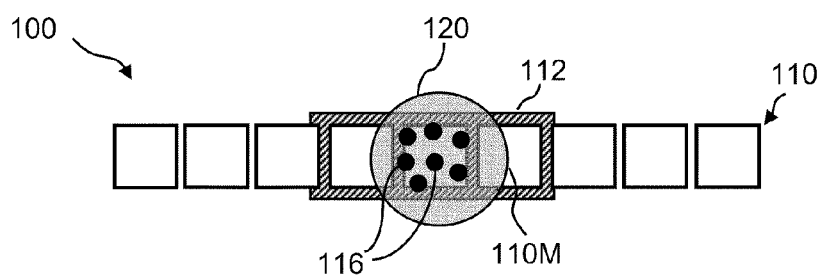

FIG. 1C shows reaction droplet 120 is incubated for a period of time sufficient to allow for the formation of capture antibody-antigen-reporter antibody complexes.

Figure 1D:
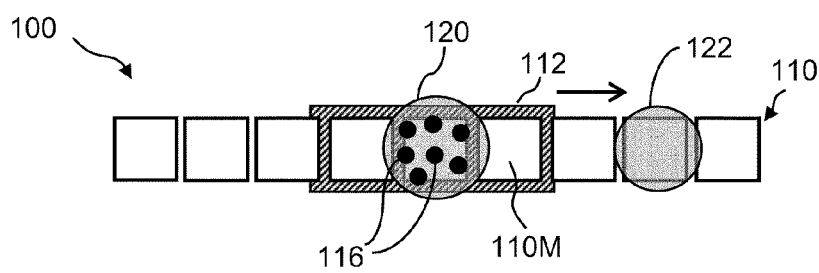

FIG. 1D shows a supernatant droplet 122 is split-off reaction droplet 120 using droplet operations. The splitting may, for example, employ a droplet splitting operation in which non-adjacent electrodes in proximity to the droplet are activated while intervening electrodes are deactivated or remain deactivated. Using droplet operations, supernatant droplet 122 may be discarded to waste or transported into a downstream process. In some cases, supernatant droplet 122 includes unbound secondary reporter antibody and antigen. If the amount of analyte captured on magnetically responsive beads 116 is insufficient for adequate measurement, one or more subsequent sample droplets 118 may be serially incubated with reaction droplet 120 that includes magnetically responsive beads 116 therein. The process shown in FIGS. 1B through 1D may be repeated any number of times to preconcentrate all the analytes from multiple sample droplets onto a single magnetically responsive bead population.

Figure 1E:
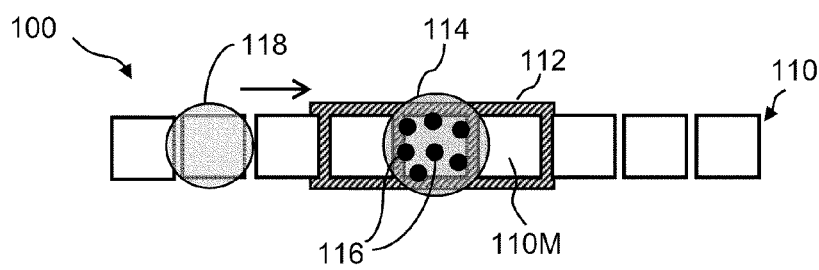

FIG. 1E shows a situation in which an assay reports a value above the linear range of the assay, so the bead-containing droplet is merged with a diluent using droplet operations and re-analyzed. One or more diluent droplets may be combined with a sample droplet to yield a diluted sample droplet 118 ready for reanalysis (not shown). In this step, a diluted sample droplet 118 is merged with a reagent droplet 114 using droplet operations to form a diluted reaction droplet. This auto-dilution sequence may be repeated any number of times sufficient to bring the concentration of analytes back within range of detection and be accurately measured. Similarly, the bead-containing droplet may be diluted by using droplet operations to combine it with one or more diluent droplets, and split outside the range of the magnetic field, such that the number of beads present in the droplet is reduced.

7.5 Incubation

Incubation protocols on a droplet actuator are generally comprised of transporting a droplet using droplet operations (e.g., a droplet that includes an antigen, primary capture antibodies conjugated to magnetically responsive beads, and secondary reporter antibodies) along electrodes arranged for conducting droplet operations, and/or by use of splitting and merging operations that are inserted between transport cycles. Transporting, splitting, and merging the droplet ensures that the beads are well distributed (i.e., mixed) within the droplet. An incubation cycle (e.g., transport, split, and merge droplet operations) may be repeated as many times as is necessary to achieve the desired exposure of beads to the surrounding droplets, for example, to achieve efficient antigen-antibody binding.

Magnetically responsive beads have a tendency to settle and form aggregates due to gravity and/or continued exposure to strong magnetic forces. These aggregates reduce the available surface area for binding and slow down reaction kinetics and, consequently, the time to result and sensitivity of the assay. Moreover, interstices in magnetically responsive bead aggregates can hold unbound species that leads to ineffective washing. This may result in less sensitive assays and inaccuracies between assays due to differing amounts of unbound species held in the interstices. Therefore, it is useful to keep the beads dispersed or resuspended during incubation and in the steps immediately following separation for further processing of the droplets away from the magnets. Resuspension of magnetically responsive beads within droplets, akin to rigorous vortexing of bench scale systems, may be achieved by moving the bead droplet back and forth and exploiting the inherent circulatory flow patterns that are developed during droplet transport.

FIGS. 2A, 2B, 2C, 2D, and 2E illustrate an incubation protocol, which is used in the immunoassays described below in Section 7.7. The figures show electrode arrangement 200 and a process of using electrode arrangement 200 for incubating where droplet 218 is moved in and out of the magnetic field of magnet 214. The method is an example of an incubation method wherein a droplet is transported using droplet operations into proximity with the magnet and then away from the magnet. Split-and-merge droplet operations are used to resuspend and mix the beads within the droplet. In the example illustrated here, the split-and-merge operations are performed away from the magnet so that resuspension of the beads is in the lateral X-Y, and vertical Z directions; however, it will be appreciated that the spit and merge operations may alternatively be performed in the presence of the magnet.

Figure 2:
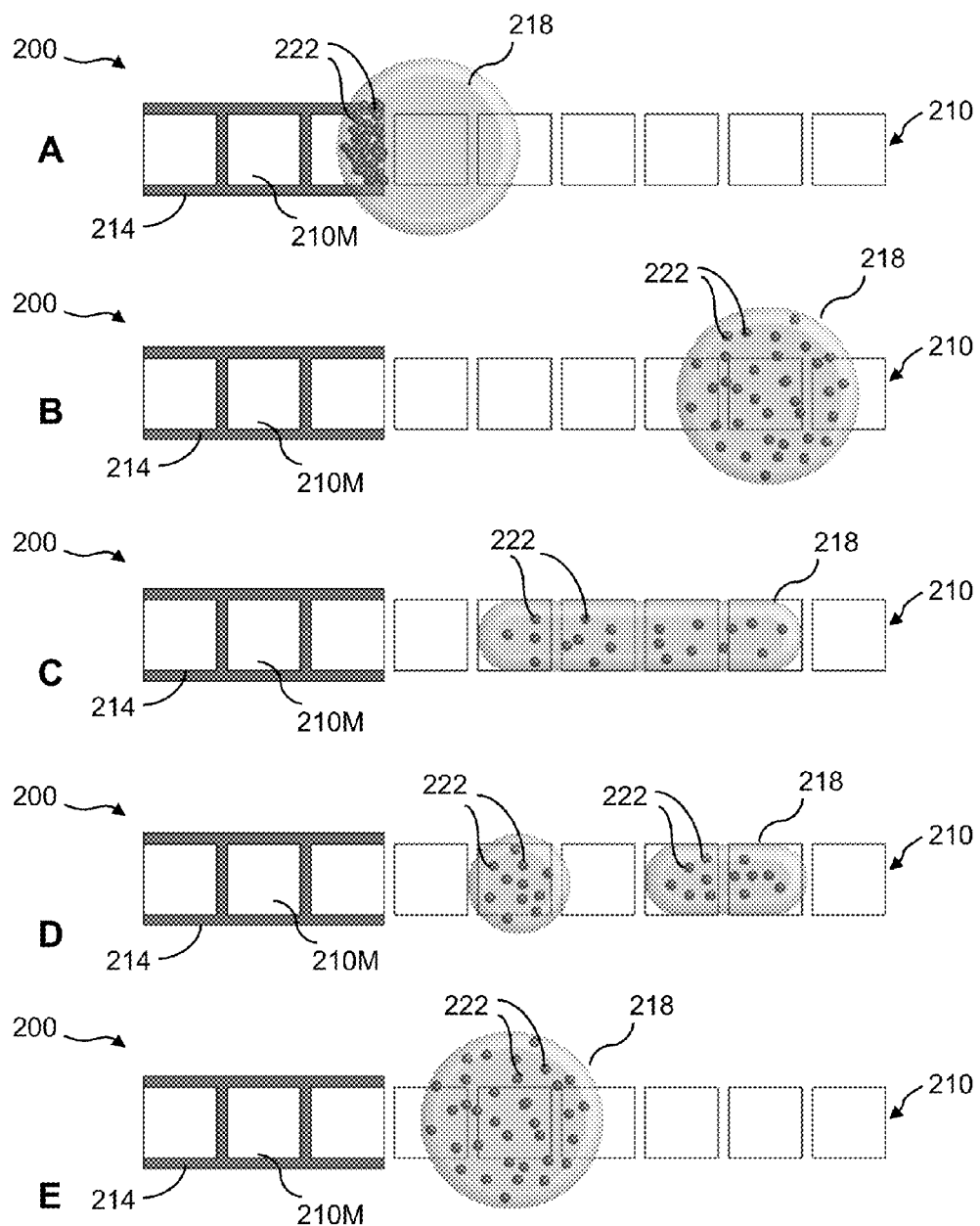
FIGS. 2A, 2B, 2C, 2D, and 2E illustrate an incubation protocol.

FIG. 2A shows a droplet 218 with beads 222 therein positioned adjacent to and slightly overlapping droplet operations electrodes 210M. As a result, magnetically responsive beads 222 are aggregated within the magnetic field of magnet 214, forming a concentration of beads at the edge of droplet 218 that is closest to magnet 214.

FIG. 2B shows droplet 218 is transported using droplet operations away from the magnetic field of magnet 214. Beads 222 are sufficiently resuspended in droplet 218.

FIGS. 2C, 2D, and 2E show the process steps of droplet elongation (i.e., formation of slug-shaped geometry), droplet splitting, and droplet merging, respectively, that are used to provide for sufficient flow of fluid within droplet 218 to resuspend and redistribute beads 222 in droplet 218. Because the split-and-merge droplet operations are performed away from the magnet, resuspension of the beads is in the X, Y, and Z directions.

7.6 Bead Washing

Washing of magnetically responsive beads, where unbound molecules are separated and removed, is one of the most critical steps in implementing an immunoassay in a digital microfluidic system. In some embodiments, washing is performed using a dilution-based merge-and-split protocol, which is repeated until the unbound material is sufficiently depleted from the supernatant to permit accurate and precise detection. Typically, as few as about 5 to 10 washes are sufficient during which addition and removal of each wash droplet results in a several-fold dilution (as opposed to a simple binary-fold dilution because under certain conditions the wash fluid displaces the supernatant fluid before the two liquids can be effectively mixed).

For protocols making use of beads, droplet with beads can be combined using droplet operations with one or more wash droplets. Then, while retaining the beads (e.g., physically or magnetically), the merged droplet may be divided using droplet operations it into two or more droplets: one or more droplets with beads and one or more droplets without a substantial amount of beads. In one embodiment, the merged droplet is divided using droplet operations into one droplet with beads and one droplet without a substantial amount of beads.

Generally, each execution of a washing protocol results in retention of sufficient beads for conducting the intended assay without unduly detrimental effects on the results of the assay. In certain embodiments, each division of the merged droplet results in retention of more than 90, 95, 97, 98, 99, 99.1, 99.2, 99.3, 99.4, 99.5, 99.6, 99.7, 99.8, 99, 99.9, 99.99, 99.999, 99.9999, 99.99999, or 99.999999 percent of beads. In other embodiments, each execution of a washing protocol to achieve a predetermined reduction in the concentration and/or amount of removed substance results in retention of more than 99, 99.1, 99.2, 99.3, 99.4, 99.5, 99.6, 99.7, 99.8, 99, 99.9, 99.99, 99.999, 99.9999, 99.99999, or 99.999999 percent of beads. In still other embodiments, the amount of retained beads is calculated and the results are adjusted accordingly.

In embodiments in which magnetically responsive beads are used, it has been found that application of a magnetic field, though useful for temporarily immobilizing beads, moving beads and/or positioning beads, sometimes results in unwanted aggregation of the beads. In one embodiment, a surfactant is included to prevent or reduce bead aggregation. Examples of surfactants suitable for this purpose include: Tween® 20, Tween® 80, Triton® X-100. Surfactants should be selected and used in amounts which reduce or eliminate bead aggregation and minimize non-specific adsorption while at the same time not resulting in significant loss of target analytes or reagents from the droplet. Another approach to eliminating or reducing clumping aggregation of beads involves the use of smaller numbers of larger beads. Any number of beads which can be contained in a droplet during one or more droplet operations may be used. For example, the number of magnetically responsive beads can range from 1 to millions, or from hundreds to several hundred thousands, or from thousands to hundreds of thousands.

Interstices in magnetic bead aggregates can hold unbound species leading to ineffective washing, yielding less sensitive assays and sometimes inaccuracies between assays due to differing amounts of unbound species held in the interstices. It may be useful to keep the beads dispersed or resuspended during incubation and in the steps immediately following separation for further processing of the droplets away from the magnets. As discussed in Section 7.5 above, resuspension and circulation of beads may be achieved by exploiting the inherent circulatory flow patterns that are developed during droplet operations, such as transport, splitting and merging.

When magnetically responsive beads are used (e.g., as capture beads) washing may be accomplished by applying a magnetic field to the droplet actuator in order to restrain or immobilize beads during a bead washing protocol. The magnetic field may be applied using an external or internal magnet. The magnetic field serves to localize the magnetically responsive beads while the surrounding liquid is exchanged through a series of merge-and-split operations, e.g., executing a wash protocol. Techniques for immobilizing magnetically responsive and/or magnetically non-responsive (or substantially non-responsive) beads during washing protocols also include the use of physical barriers.

Examples of droplet actuator techniques for immobilizing magnetically responsive beads and/or magnetically non-responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

7.7 Immunoassays

FIGS. 3A, 3B, 3C, 3D, and 3E illustrate top views of an electrode arrangement 300 of a droplet actuator and show a process of performing an immunoassay on a digital microfluidic platform. The drawings are not to scale; sizes of the electrodes may be adjusted by one of skill in the art. Electrode arrangement 300 may include a reagent dispensing electrode 310 and a wash buffer dispensing electrode 312. Reagent dispensing electrode 310 and wash buffer dispensing electrode 312 may be arranged in association with an arrangement of droplet operations electrodes 314, such as electrowetting electrodes arranged for conducting droplet operations. The droplet operations are conducted atop the electrodes on a droplet operations surface. A droplet may be dispensed from either dispensing electrode onto the arrangement of droplet operations electrodes 314. A magnet 316 is arranged in proximity to droplet operations electrodes 314. In particular, magnet 314 is arranged such that certain droplet operations electrodes 314 (e.g., 3 droplet operations electrodes 314M) are sufficiently within the magnetic field of magnet 316 that magnetically responsive beads within a droplet atop electrodes 314M will be immobilized or restrained by magnet 316. Magnet 316 may, for example, be a permanent magnet or an electromagnet.

A sample droplet 318 may be positioned on a droplet operations surface atop electrodes 314 and subject to droplet operations mediated by electrodes 314. Sample droplet 318 may, for example, potentially contain an analyte of interest, such as a cardiac marker, to be evaluated by an immunoassay. An example of a process of performing an immunoassay on a digital microfluidic platform may include, but is not limited to, the following steps, which may be electrode mediated using droplet operations on a droplet operations surface, such as within a droplet operations gap.

Figure 3:
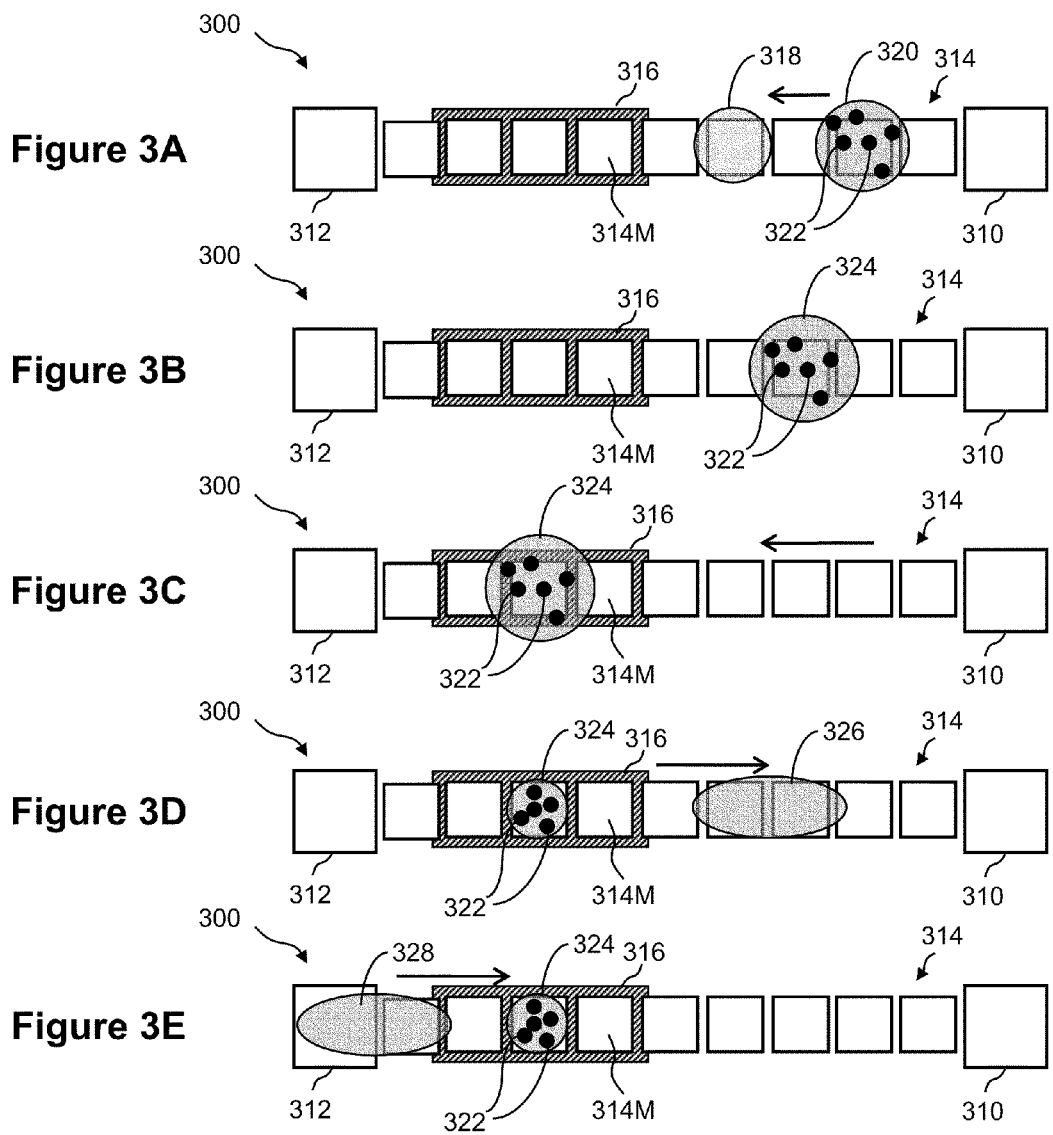
FIGS. 3A, 3B, 3C, 3D, and 3E illustrate top views of an electrode arrangement of a droplet actuator and show a process of performing an immunoassay on a digital microfluidic platform.

FIG. 3A shows reagent droplet 320, which has been dispensed by reagent dispensing electrode 310. Reagent droplet 320 includes magnetically responsive beads 322. Magnetically responsive beads 322 include primary capture antibodies. Reagent droplet 320 contain may also include blocking proteins and/or secondary reporter antibodies. Using droplet operations, reagent droplet 320 is merged with sample droplet 318 using droplet operations to form reaction droplet 324, shown in FIG. 3B.

FIG. 3B shows reaction droplet 324 incubated for a period of time sufficient to permit formation of capture antibody-antigen-reporter antibody complexes.

FIG. 3C shows reaction droplet 324 with beads 322 therein transported using droplet operations onto the droplet operations surface atop droplet operations electrodes 314M. Because beads 322 are magnetically responsive, they are attracted to and held or immobilized by the magnetic field.

FIG. 3D shows a supernatant droplet 326 split off from reaction droplet 324 and discarded to waste (not shown). The splitting may, for example, employ a droplet splitting operation in which non-adjacent electrodes in proximity to the droplet are activated while intervening electrodes are deactivated or remain deactivated. Because the magnetically responsive beads 322 are immobilized, they are restrained during the droplet splitting exercise and as a result, droplet 324 retains the magnetically responsive beads 322 and antibody-antigen-reporter antibody complexes thereon, while supernatant droplet 326 includes unbound secondary reporter antibodies and antigen.

FIG. 3E shows a wash buffer droplet 328 dispensed from wash dispensing electrode 312 and merged with reaction droplet 324 using droplet operations. Residual unbound material (i.e., secondary reporter antibody and antigen) is washed away using a merge-and-split droplet operations based wash protocol.

The steps shown in FIG. 3D and FIG. 3E may be repeated any number of times (e.g., 5 times) sufficient for removal of unbound material.

A chemiluminescence substrate droplet may be combined using droplet operations with the droplet including the washed magnetically responsive beads, and the amount of analyte present may be detected (not shown in figure).

7.8 Examples

The ensuing examples are provided to further illustrate the invention.

7.8.1 Calibrators and Reagents

For detection of cardiac markers cTnI, Mb, and CK-MB, Beckman Access kits were used for calibrators (standards) and reagents. Any preparation of reagents and/or calibrators was performed on-bench prior to loading on a droplet actuator. A total of six calibrators (S0, S1, S2, S3, S4, and S5) are available in the Beckman Access kits. For experiments performed on the droplet actuator cartridge, a seventh calibrator (S1.5) was prepared by mixing calibrators S1 and S2 in equal proportions.

The Beckman Access kit for cTnI includes primary antibody on magnetically responsive beads (reagent A), blocking antibody (reagent B), and reporter antibody (reagent C). To prepare the reagents for loading on the droplet actuator, a 2.4-µL aliquot of supernatant from a 6-µL aliquot of reagent A was removed and replaced with 2.4-µL of reagent B (reagent D). All calibrators were used as supplied.

The Beckman Access kit for Mb includes primary antibody on beads (reagent A) and reporter antibody (reagent B). Reagents were used as supplied. All calibrators were diluted 100× in DPBS buffer (Gibco).

The Beckman Access kit for CKMB includes primary antibody on magnetically responsive beads (reagent A), blocking antibody (reagent B), and reporter antibody (reagent C). To prepare the reagents for loading on the droplet actuator, a 3.0-µL aliquot of supernatant from a 6-µL aliquot of reagent A was removed and replaced with 3.0 µL of reagent B (reagent E). All calibrators were used as supplied.

7.8.2 Droplet Actuator Setup

Figure 4:
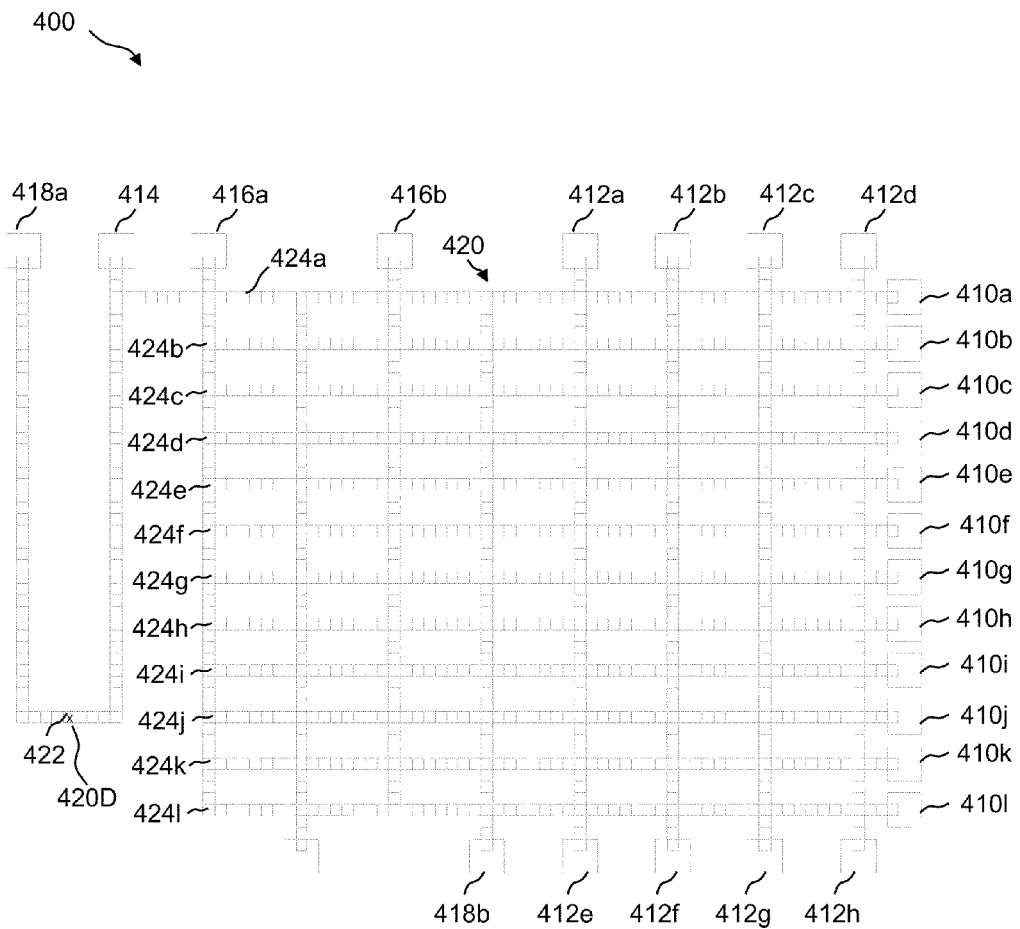
FIG. 4 illustrates a top view of a droplet actuator showing an electrode layout that is configured for multiplexed immunoassays for detection of cardiac markers.

FIG. 4 illustrates a top view of a droplet actuator showing electrode layout 400 configured for multiplexed immunoassays for detection of cardiac markers. Electrode layout 400 includes multiple reservoirs formed between a bottom substrate (not shown) and a top substrate (not shown) that are separated by a gap. The gap is filled with a silicone oil filler fluid. In one embodiment, the bottom substrate may be a printed circuit board (PCB). The top substrate may be formed of indium tin oxide (ITO) glass. A spacer is provided between the bottom substrate (not shown) and top substrate to determine the height of the gap therebetween. The spacer height may be, for example, about 185 µm. A well plate (not shown) is provided atop the top substrate. The well plate may include one or more wells for containing a larger quantity of fluid for delivering liquid through a fluid path into the gap of the droplet actuator.

Electrode layout 400 includes multiple dispensing electrodes, which may, for example, be allocated as sample dispensing electrodes 410, i.e., sample dispensing electrodes 410a through 410l, for dispensing sample fluid (e.g., Beckman Access Calibrators); reagent dispensing electrodes 412, i.e., reagent dispensing electrodes 412a through 412h, for dispensing different reagent fluids (e.g., primary antibody on beads, blocking antibody, reporter antibody); substrate dispensing electrode 414, which is associated with the input well for the detection substrate (e.g., APS-5); wash buffer dispensing electrodes 416a and 416b, for dispensing wash buffer fluids; and waste collection electrodes 418a and 418b for receiving spent reaction droplets (e.g., wash buffer waste droplets). Each of the dispensing and collecting electrodes is supplied by or feeds to a well formed in the top substrate of the droplet actuator, and a fluid path connects the dispensing and collecting electrodes to the associated well. A single large washing well is associated with two fluid paths feeding two wash buffer dispensing electrodes 416a and 416b. Sample dispensing electrodes 410, reagent dispensing electrodes 412, substrate dispensing electrode 414, wash buffer dispensing electrodes 416, and waste collection electrodes 418 are interconnected through an arrangement of droplet operations electrodes 420 that are arranged for conducting droplet operations. The droplet operations are conducted atop the electrodes on a droplet operations surface. A path of droplet operations electrodes 420 extending from each sample dispensing electrode 410 forms individual reaction lanes 424, i.e., reaction lanes 424a through 424l. A detection spot 422 is positioned in proximity of a certain droplet operations electrode 420D. Detection spot 422 is aligned with a Photomultiplier Tube (PMT) 120-s photon counter with an attached lens.

Figure 5:
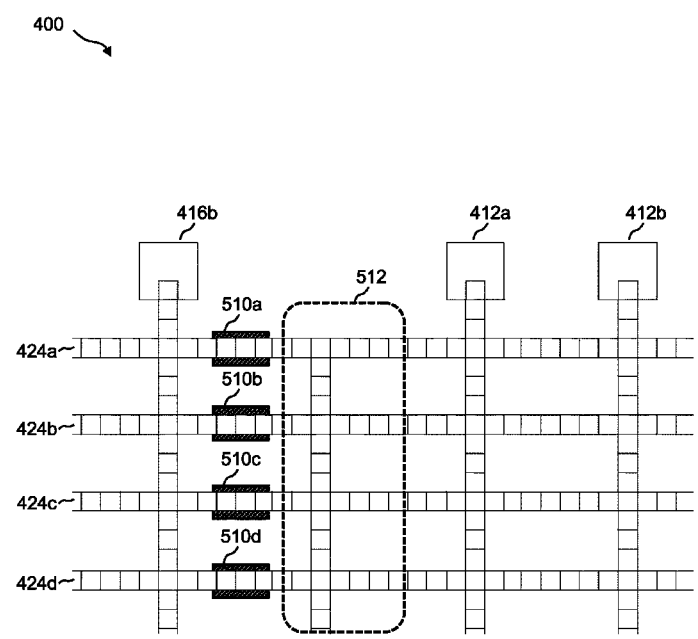
FIG. 5 illustrates an expanded view of a region of the electrode layout of FIG. 4.

FIG. 5 illustrates an expanded view of a region of electrode layout 400 of FIG. 4. A magnet 510 (e.g., 510a, 510b, 510c, 510d) is positioned in proximity to an incubation region 512 on each reaction lane 424 (e.g., reaction lanes 424a, 424b,

424c, and 424d). In this example, magnet 510 is an NdFeB, grade N42 with Ni—Cu—Ni plating/coating with a pull force of 1.06 lbs and a surface field of 2920 Gauss (Product #B221; K&J Magnetics, Inc., Jamison, Pa.). Magnets 510 are positioned below the droplet actuator cartridge and span 3 droplet operations electrodes 420. The distance between the top of magnets 510 and the base of the droplet actuator cartridge is, for example, about 500 µm. Lane to lane (e.g., reaction lane 424a and 424b) distance between magnets 510 (e.g., magnet 510a and magnet 510b) is, for example, about 4.5 mm.

7.8.3 Assay Protocol

Silicone oil filler fluid, assay reagents and sample fluids were loaded onto the droplet actuator that includes electrode layout 400 through aligned openings in the top substrate (not shown). The loading order and volumes loaded were as follows:

1. 1.8 mL of 0.1% Triton X-15 in 2 cSt silicone oil (filler fluid) was loaded through a well aligned with wash buffer dispensing electrode 416b.
2. 1.4 mL of wash buffer (0.05M TRIS, 0.1 M NaCl, 0.1 mg/mL BSA, 0.02% Tween20, pH 9.5) was loaded in a well aligned with wash buffer dispensing electrodes 416a and 416b.
3. 200 µL of wash buffer was loaded in a well aligned with wash buffer dispensing electrode 416a (detection wash well).
4. 2.2 µL of each Calibrator was loaded onto separate sample dispensing electrodes 410.
5. 4.2 µL of each assay reagent (i.e., primary antibody on magnetically responsive beads, blocking antibody, and reporter antibody) was loaded onto separate reagent dispensing electrodes 412. Reagent A that includes magnetically responsive beads was loaded in a reagent reservoir located farthest away from the wash reservoir (e.g., reagent dispensing electrode 412d).
6. After the eighth wash in the assay protocol (detailed below), 175 µL of detection substrate APS-5 was loaded in a well aligned with substrate dispensing electrode 414.

All steps in the protocol were accomplished in a droplet operations gap of a droplet actuator using electrowetting-mediated droplet operations effected by activating and deactivating the electrodes. The assay protocol included dispensing and merging two 1X droplets of calibrator with one 1X droplet of a first reagent (reagent 1) that includes the magnetically responsive beads. For cTnI and CKMB immunoassays, reagent 1 was the mixture of reagents A and B as described above. For Mb immunoassays, reagent 1 was reagent A as described above.

After a 3-minute incubation (described below), the 3X droplet slug was transported using droplet operations to the magnet and one 1X droplet of supernatant was split-off and discarded to waste. To achieve this result the 3X incubation droplet was transported using droplet operations atop the magnet to immobilize the magnetically responsive beads, and a 1X supernatant droplet was split off of each of the 3X droplets using a droplet splitting operation and transported using droplet operations into a waste reservoir on the well plate of the droplet actuator. The supernatant droplets were transported using droplet operations into contact with a capillary fluid path leading from the droplet actuator gap into the waste reservoir, and capillary forces caused the supernatant droplets to flow through the capillary fluid path into the waste reservoir.

One 1X droplet of a second reagent (reagent 2) was dispensed and merged using droplet operations with the remaining 2X droplet at the magnet. For cTnI and CKMB, reagent 2 was reagent C as described above. For Mb, reagent 2 was reagent B as described above.

After a 2-minute incubation, the 3X droplet was transported using droplet operations to the magnet as described above and one 1X droplet of supernatant was split-off using droplet operations and discarded to waste. At the magnet the 2X droplet was subjected to 11 washes using 2X droplets.

The 2X droplet was reduced in volume (i.e., one 1X droplet of supernatant was split-off) to a 1X droplet that contained all beads. The bead containing droplet was then merged with one 1X droplet of APS-5 substrate using droplet operations and transported using droplet operations to the detection spot. Detection of the chemiluminescent signal was performed for 5 seconds with a 250 ms integration time and a 4 Hz sample rate. All data was reported in counts/second.

Dispensing protocols used in the assay were as follows. For sample and reagent dispensing (i.e., dispensing a 1X droplet), a fluid finger was extended from the dispensing electrode by sequentially activating three droplet operations electrodes: beginning with activating a first droplet operations electrode embedded in the dispensing electrode, then activating a second droplet operations electrode adjacent to the first droplet operations electrode, then activating a third droplet operations electrode in the sequence. The second droplet operations electrode was then deactivated to split the finger, leaving a newly formed droplet on the third droplet operations electrode. Prior to dispensing, electrodes were primed by repeatedly extending and retracting the droplet finger prior to splitting off the sub-droplet.

For 2X wash droplet dispensing, a fluid finger was extended from the dispensing electrode by sequentially activating three droplet operations electrodes: beginning with activating a first droplet operations electrode embedded in the dispensing electrode, then activating a second droplet operations electrode adjacent to the first droplet operations electrode, then activating a third droplet operations electrode in the sequence, then activating a fourth droplet operations electrode in the sequence. The second droplet operations electrode was then deactivated to split the finger, leaving a newly formed 2X droplet on the third and fourth droplet operations electrodes. The 2X droplet was then transported using droplet operations by sequentially activating two adjacent droplet operations electrode at a time along the desired transport path. Prior to dispensing, electrodes were primed by repeatedly extending and retracting the droplet finger prior to splitting off the sub-droplet.

7.8.4 Results

Figure 6A:
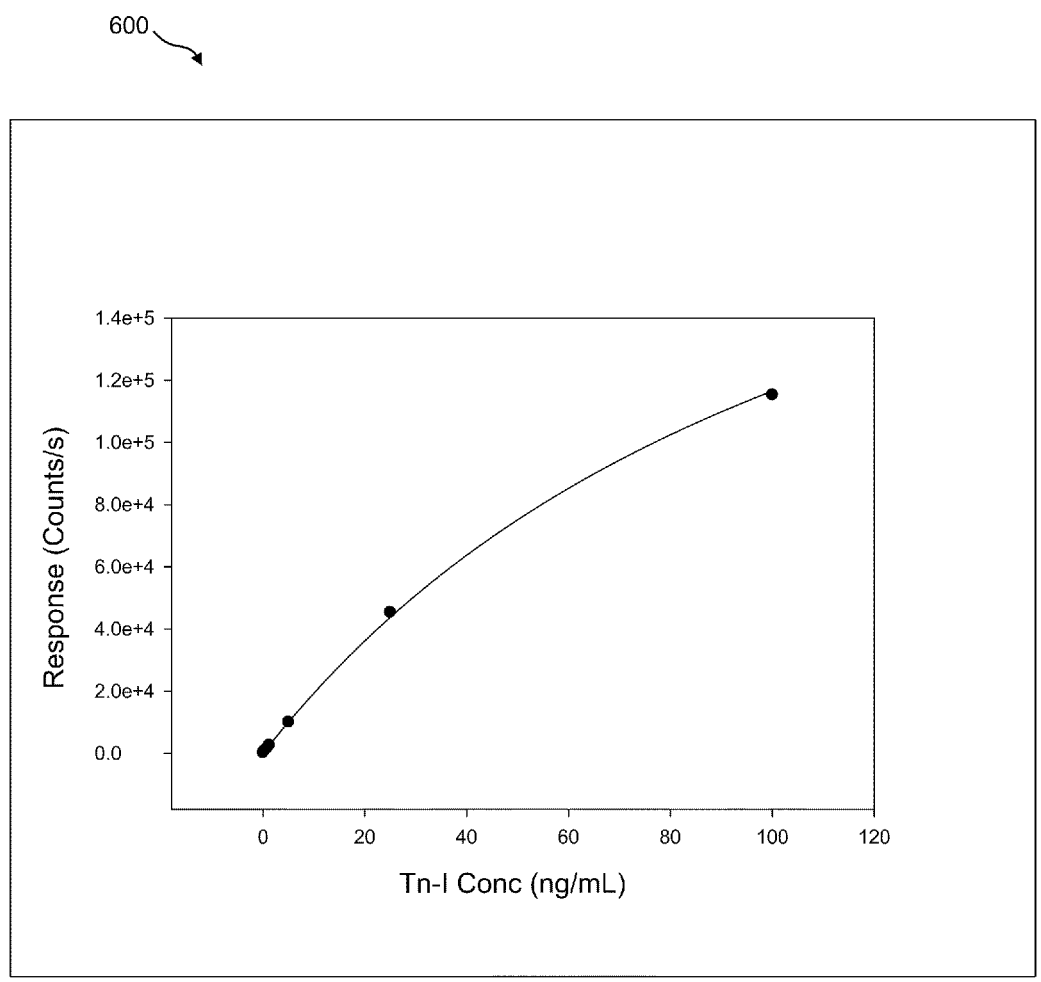
FIGS. 6A and 6B show a calibration curve and recovery chart, respectively, for cardiac troponin (cTn)
Figure 6B:
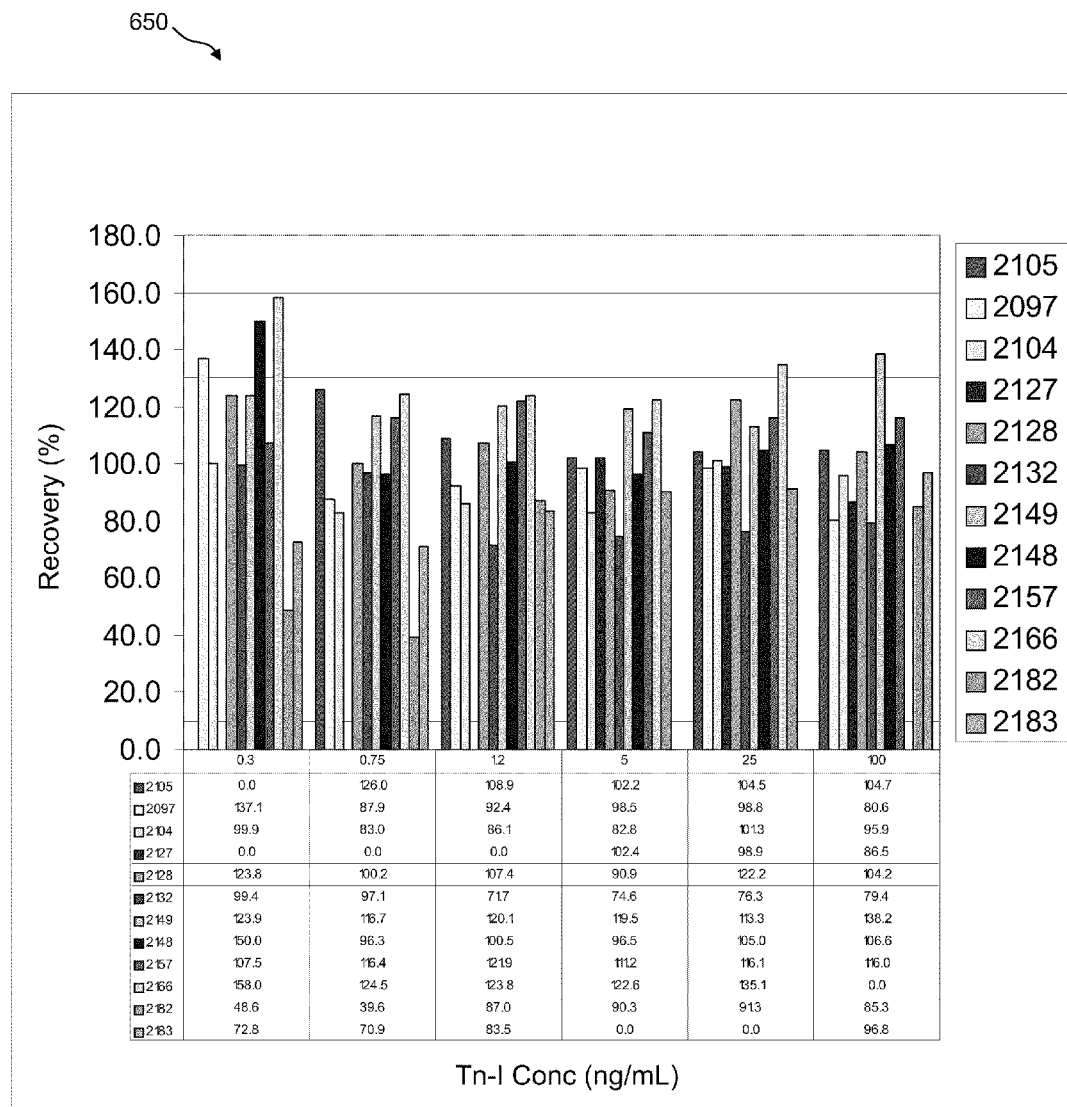
Figure 7A:
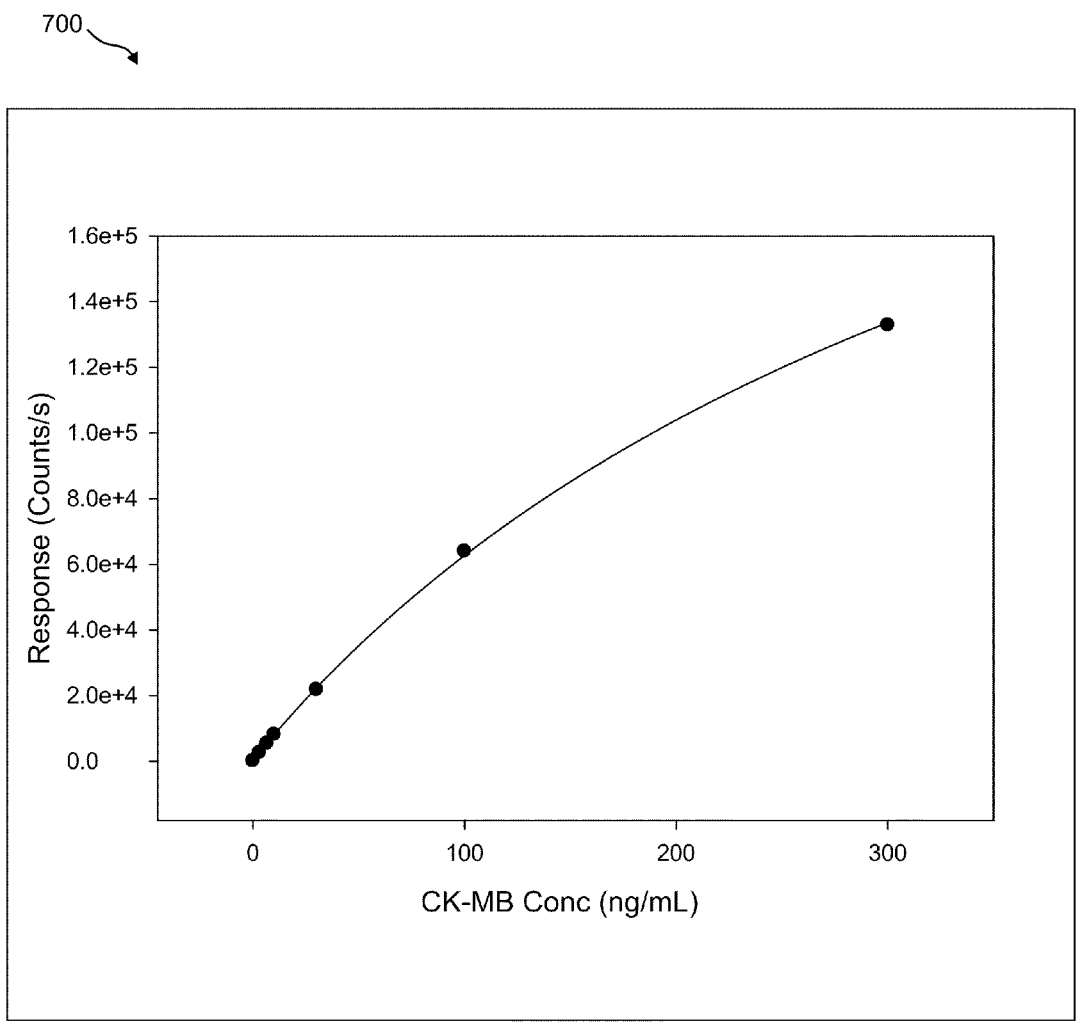
FIGS. 7A and 7B show a calibration curve and recovery chart, respectively, for cardiac marker, creatine kinase MB (CK-MB)
Figure 7B:
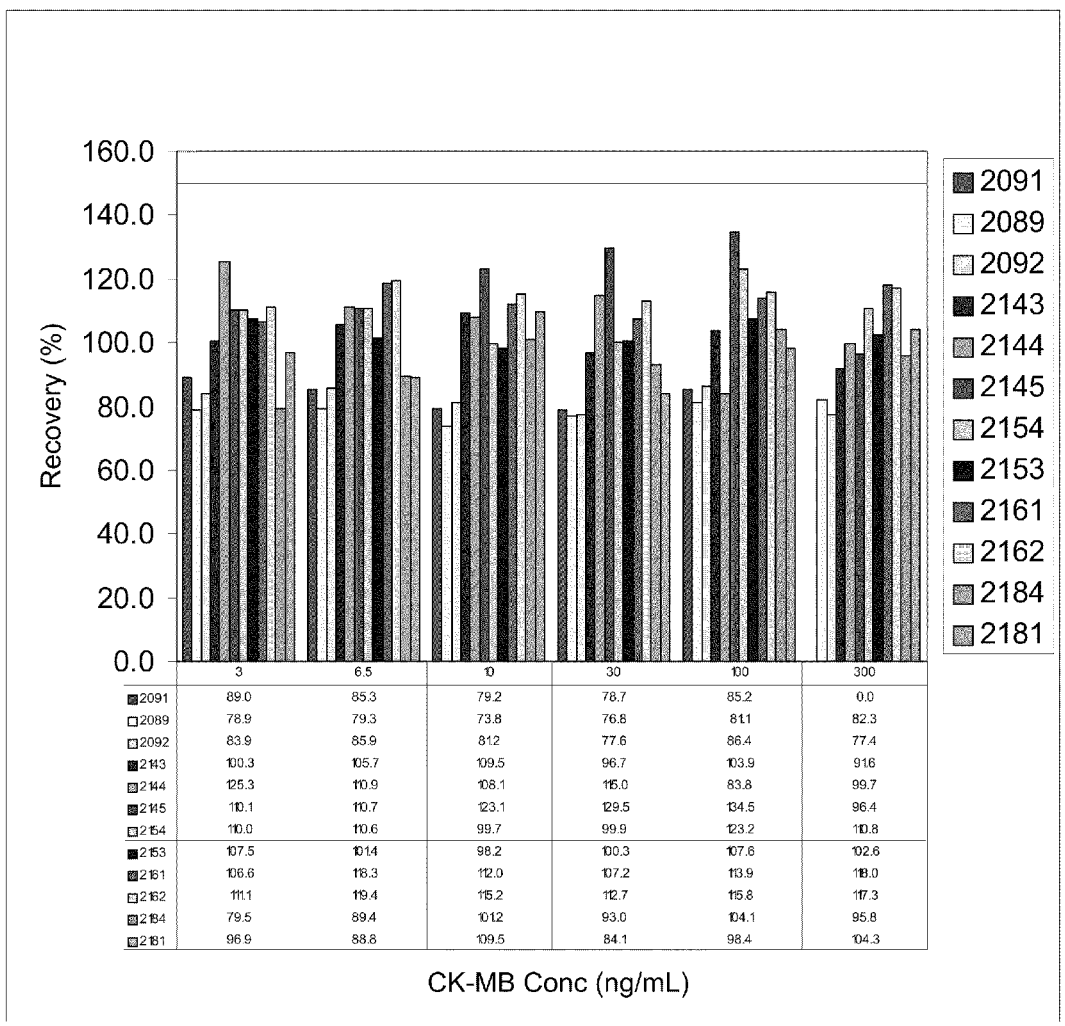
Figure 8A:
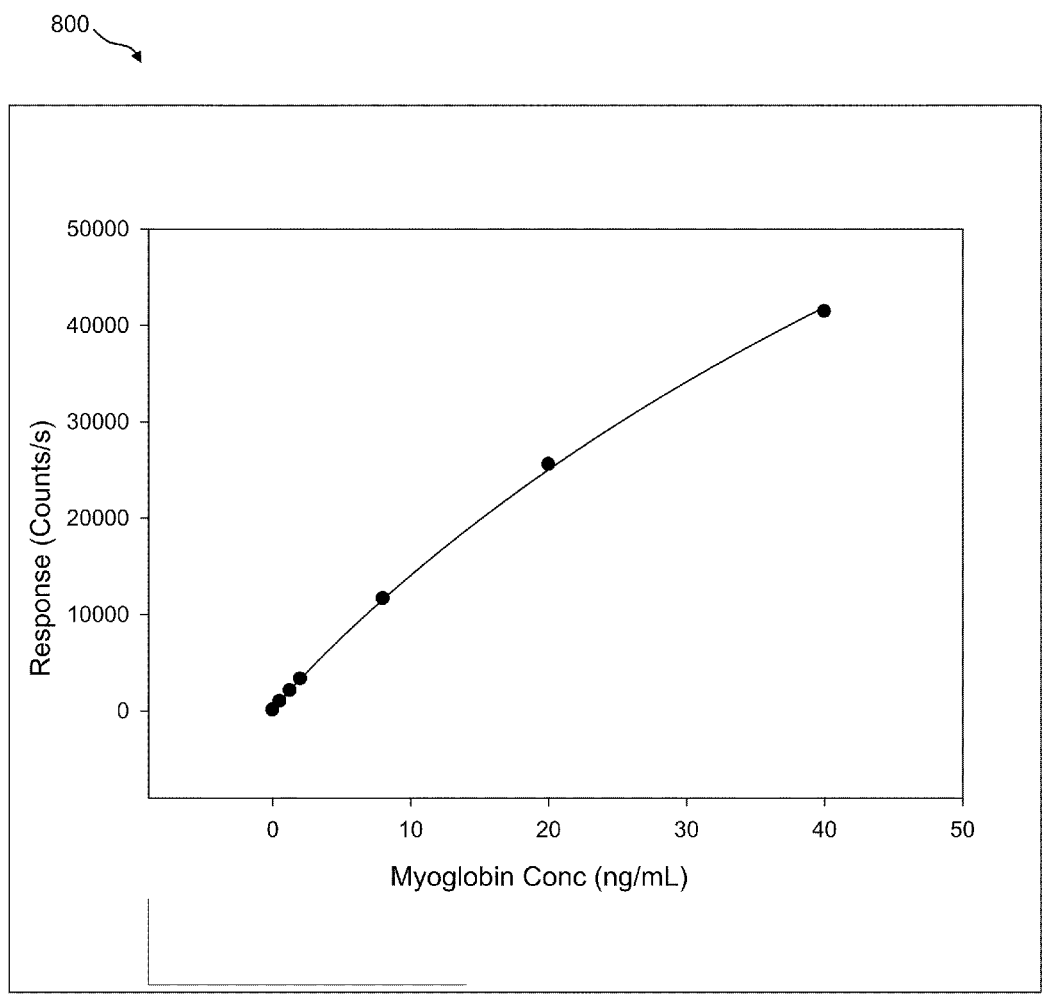
FIGS. 8A and 8B show a calibration curve and recovery chart, respectively, for myoglobin.
Figure 8B:
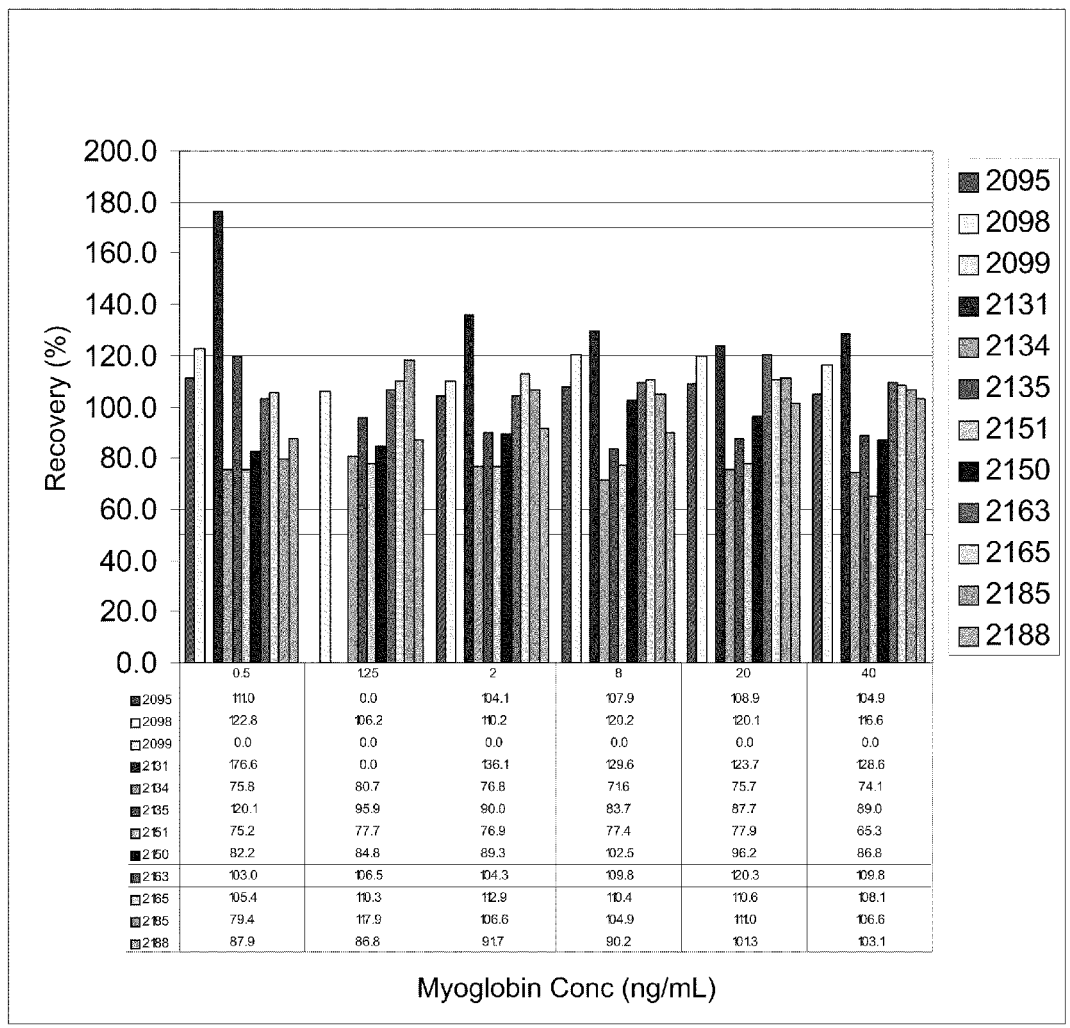

For each cardiac marker, the assay protocol described above was performed on twelve different cartridges. Average responses from each calibrator from these twelve cartridges were used for generating a single calibration curve that was plotted in SigmaPlot using a reciprocal y-square weighting. FIGS. 6A, 7A, and 8A show the calibration curves for cTn-I, CK-MB, and Myoglobin respectively. Individual responses from each cartridge were fit back into the corresponding calibration curve to calculate the recovery percentages as a function of the calibrator concentration. FIGS. 6B, 7B, and 8B show the recovery percentages for cTn-I, CK-MB, and Myoglobin respectively. A data table showing the individual responses from the calibrators for all twelve cartridges is provided in each of these figures below the bar graphs. The legend to the right of the graph shows the twelve cartridge numbers and is shaded to match the recoveries in the bar graph. The first column of the data table provides the cartridge numbers again and the top row of the table (also serves as the x-axis for the graph) indicates the concentration of the calibrators.

7.9 System

As will be appreciated by one of skill in the art, the invention may be embodied as a method, system, or computer program product. The droplet actuator may be provided as an integrated system, or may be provided as a cartridge that may be coupled with an instrument to provide an operating droplet actuator system. For example, the instrument may include processors and electrical connections for providing power and electronic signals to and from the droplet actuator. The instrument and the droplet actuator may include complimentary mating alignment features to ensure proper positioning, e.g., with respect to electrical contacts on the system and on the droplet actuator or with respect to sensors on the system and corresponding detection spots on the droplet actuator. In certain embodiments, the mating alignment features align the droplet actuator with various functional elements, such as heaters, magnets, and detection elements.

Software controlling the analysis protocol may be executed automatically or upon prompting by an operator. The assay may proceed to completion without operator intervention. Using droplet operations, sample and reagent droplets are dispensed and subjected to droplet operations according to a protocol on a droplet operations surface of the droplet actuator. Examples of suitable reagents include capture beads, blocking reagents, and secondary reporter antibodies (e.g., reporter antibodies for fluorescence detection), as required by the analysis protocol.

Accordingly, various aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

The system may output information, such as an identification of the presence and/or quantity of analyte in a sample or information which is extrapolated from the measured results of the assay. Output information may, for example, include diagnostic or prognostic information relating to one or more cardiac conditions; and/or information relating to a subject's risk of one or more cardiac conditions; and/or information about managing a subject's risk of or having one or more cardiac conditions. The output information may describe or provide an assessment of one or more acute or chronic cardiac conditions. For example, the information may include a quantitative or qualitative assessment of AMI or of risk of AMI. Output from a system of the invention may include information confirming AMI and/or ruling out AMI. Output information from cardiac marker testing according to the invention may include information useful for triaging patients with chest pain. Output information from cardiac marker testing according to the invention may include information useful for assessing reperfusion status following thrombolytic therapy. Other examples of output information will be apparent to the skilled artisan in view of the present disclosure.

Concluding Remarks

The foregoing detailed description of embodiments refers to the accompanying drawings, which illustrate specific embodiments of the invention. Other embodiments having different structures and operations do not depart from the scope of the invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the invention may be changed without departing from the scope of the invention. Furthermore, the foregoing description is for the purpose of illustration only, and not for the purpose of limitation.

We claim:

1. A method of assaying a cardiac marker in a biological sample from a subject, the method comprising:
   (a) providing a droplet actuator;
   (b) loading the biological sample and assay reagents on the droplet actuator;
   (c) executing droplet operations to create sample droplets from the sample and reagent droplets from the reagents on the droplet actuator; and
   (d) executing droplet operations using the sample droplets and reagent droplets to produce a detectable signal indicative of the quantity of the cardiac marker in the biological sample the method further comprising, prior to loading the sample on the droplet actuator, binding cardiac markers of interest to capture beads, and loading the capture beads onto the droplet actuator.

2. The method of claim 1 comprising conducting assays for two or more cardiac markers in parallel.

3. The method of claim 1 comprising conducting assays for three or more cardiac markers in parallel.

4. The method of claim 1 comprising conducting assays for four or more cardiac markers in parallel.

5. The method of claim 1 wherein the cardiac marker is selected from the group consisting of cardiac troponin, creatine kinase, aspartate transaminase, lactate dehydrogenase, and Mb.

6. The method of claim 1 wherein the cardiac marker is selected from the group consisting of AST, ANP, BNP, proBNP, NT-proBNP, cTn, cTnI, cTnC, cTnT, cTn isoforms, CRP, CKMB, CNP, CSC, FABP, GPBB, IMA, LDH, MPO, Mb, PIGF, PAPPA, sCD40 ligand, and fragments, precursors, and isoforms of the foregoing.

7. The method of claim 1 wherein loading the biological sample to producing a detectable signal is accomplished in a time that is less than about 10 minutes.

8. The method of claim 1 wherein the biological sample loaded onto the droplet actuator has a volume ranging from about 0.001 to about 100 µL.

9. The method of claim 1 wherein the biological sample loaded onto the droplet actuator has a volume ranging from about 0.01 to about 50 µL.

10. The method of claim 1 wherein the biological sample loaded onto the droplet actuator has a volume ranging from about 0.1 to about 25 µL.

11. The method of claim 1 wherein the biological sample loaded onto the droplet actuator has a volume ranging from about 1 to about 20 µL.

12. The method of claim 1 further comprising providing an output indicative of the quantity of cardiac marker(s).

13. The method of claim 12 further comprising using the output to assess whether a subject has recently experienced or is contemporaneously experiencing an acute myocardial infarction.)

14. The method of claim 12 further comprising using the output as a prognostic indicator.

15. The method of claim 1 wherein the beads are magnetically responsive.

16. The method of claim 1 wherein the beads are not substantially magnetically responsive.

17. The method of claim 1 further comprising subjecting the capture beads to a droplet-based wash protocol.

18. The method claim 2 wherein the assays for each cardiac marker are run in multiplicate on a single droplet actuator.

19. The method claim 2 wherein each assay is run on a separate lane of the droplet actuator.

20. The method of claim 1 wherein the assay produces spike recovery data using physiological samples such as plasma and serum.

21. The method of claim 1 wherein less than about 5 minutes elapses from loading the sample to producing a detectable signal.

22. The method of claim 1 wherein less than about 5 minutes elapses from loading the sample to producing a detectable signal for 2 or more cardiac markers.

23. The method of claim 1 wherein less than about 5 minutes elapses from loading the sample to producing a detectable signal for 3 or more cardiac markers.

24. A method of assaying a cardiac marker in a biological sample from a subject, the method comprising:
   (A) providing a droplet actuator;
   (B) loading the biological sample and assay reagents on the droplet actuator;
   (C) executing droplet operations to create sample droplets from the sample and reagent droplets from the reagents on the droplet actuator; and
   (D) executing droplet operations using the sample droplets and reagent droplets to produce a detectable signal indicative of the quantity of the cardiac marker in the biological sample wherein step (D) comprises using one or more droplet operations in the execution of the following steps:
     (a) combining a sample droplet with a reagent droplet comprising:
       (i) beads comprising primary capture antibodies; and
       (ii) reporter secondary antibodies;
       to produce an assay droplet;
     (b) incubating the assay droplet for a time sufficient to allow for the formation of capture antibody-antigen-reporter antibody complexes;
     (c) executing a droplet-based wash protocol to remove unbound material from the beads to yield a washed-beads droplet;
     (d) combining a chemiluminescence substrate droplet with the washed beads droplet; and
     (e) detecting the quantity of the cardiac marker(s).

25. The method of claim 24 wherein step 19(c) is repeated until the unbound material is sufficiently depleted to permit accurate and precise detection of the cardiac marker.

26. The method of claim 24 wherein:
   (a) step 19(c) is repeated less than about 10 times using droplets ranging from about 1X to about 5X the sample droplet; and
   (b) upon completion of step 19(c), the unbound material is sufficiently depleted to permit accurate and precise detection of the cardiac marker.

27. The method of claim 24 wherein:
   (a) step 19(c) is repeated less than about 5 times using droplets ranging from about 1X to about 5X the sample droplet; and
   (b) upon completion of step 19(c), the unbound material is sufficiently depleted to permit accurate and precise detection of the cardiac marker.

28. The method of claim 24 wherein bead retention in step 19(c) is substantially complete.

29. The method of claim 24 wherein:
(a) the beads are magnetically responsive;
(b) step 19(c) comprises using a magnet to immobilize the beads as needed during droplet-based wash protocol; and
(c) following step 19(c), the washed-beads droplet is transported away from the magnet without substantial loss of beads.

30. The method of claim 24 wherein the incubating step comprises serially incubating multiple sample droplets with a single bead population to pre-concentrate cardiac markers from multiple sample droplets onto a single bead population.

31. The method of claim 24 wherein:
(a) less than about 600 seconds elapses from loading the sample to producing a detectable signal; and
(b) the assay droplet is incubated for a time that ranges from about 30 seconds to about 300 seconds.

32. The method of claim 24 wherein:
(a) less than about 600 seconds elapses from loading the sample to producing a detectable signal; and
(b) the assay droplet is incubated for a time that ranges from about 60 seconds to about 240 seconds.

33. The method of claim 24 wherein:
(a) less than about 600 seconds elapses from loading the sample to producing a detectable signal; and
(b) the assay droplet is incubated for a time that is less than about 240 seconds.

34. The method of claim 24 wherein:
(a) less than about 300 seconds elapses from loading the sample to producing a detectable signal; and
(b) the assay droplet is incubated for a time that ranges from about 30 seconds to about 180 seconds.

35. The method of claim 24 wherein:
(a) less than about 300 seconds elapses from loading the sample to producing a detectable signal; and
(b) the assay droplet is incubated for a time that ranges from about 60 to about 150 seconds.

36. The method of claim 24 wherein:
(a) less than about 300 seconds elapses from loading the sample to producing a detectable signal; and
(b) the assay droplet is incubated for a time that is less than about 120 seconds.

37. The method of claim 24 wherein:
(a) less than about 240 seconds elapses from loading the sample to producing a detectable signal; and
(b) the assay droplet is incubated for less than about 120 seconds.

38. The method of claim 24 wherein:
(a) less than about 600 seconds elapses from loading the sample to producing a detectable signal; and
(b) the droplet-based wash protocol is completed in a time that ranges from about 30 seconds to about 300 seconds.

39. The method of claim 24 wherein:
(a) less than about 600 seconds elapses from loading the sample to producing a detectable signal; and
(b) the droplet-based wash protocol is completed in a time that ranges from about 60 seconds to about 300 seconds.

40. The method of claim 24 wherein:
(a) less than about 600 seconds elapses from loading the sample to producing a detectable signal; and
(b) the droplet-based wash protocol is completed in a time that is less than about 300 seconds.

41. The method of claim 24 wherein:
(a) less than about 300 seconds elapses from loading the sample to producing a detectable signal; and
(b) the droplet-based wash protocol is completed in a time that ranges from about 30 seconds to about 240 seconds.

42. The method of claim 24 wherein:
(a) less than about 300 seconds elapses from loading the sample to producing a detectable signal; and
(b) the droplet-based wash protocol is completed in a time that ranges from about 30 seconds to about 180 seconds.

43. The method of claim 24 wherein:
(a) less than about 300 seconds elapses from loading the sample to producing a detectable signal; and
(b) the droplet-based wash protocol is completed in a time that is less than about 180 seconds.

44. The method of claim 24 wherein:
(a) less than about 600 seconds elapses from loading the sample to producing a detectable signal; and
(b) the detecting is completed in a time that ranges from about 30 seconds to about 180 seconds.

45. The method of claim 24 wherein:
(a) less than about 600 seconds elapses from loading the sample to producing a detectable signal; and
(b) the detecting is completed in a time that ranges from about 60 seconds to about 150 seconds.

46. The method of claim 24 wherein:
(a) less than about 600 seconds elapses from loading the sample to producing a detectable signal; and
(b) the detecting is completed in a time that is less than about 150 seconds.

47. The method of claim 24 wherein:
(a) less than about 300 seconds elapses from loading the sample to producing a detectable signal; and
(b) the droplet-based wash protocol is completed in a time that ranges from about 30 seconds to about 180 seconds.

48. The method of claim 24 wherein:
(a) less than about 300 seconds elapses from loading the sample to producing a detectable signal; and
(b) the detecting is completed in a time that ranges from about 60 seconds to about 180 seconds.

49. The method of claim 24 wherein:
(a) less than about 300 seconds elapses from loading the sample to producing a detectable signal; and
(b) the detecting is completed in a time that is less than about 180 seconds.

50. The method of claim 24 wherein:
(a) the assay droplet is incubated for a time that ranges from about 30 seconds to about 300 seconds;
(b) the droplet-based wash protocol is completed in a time that ranges from about 30 seconds to about 300 seconds; and
(c) the detecting is completed in a time that ranges from about 30 seconds to about 180 seconds.

51. The method of claim 24 wherein:
(a) the assay droplet is incubated for a time that ranges from about 60 seconds to about 240 seconds;
(b) the droplet-based wash protocol is completed in a time that ranges from about 60 seconds to about 300 seconds; and
(c) the detecting is completed in a time that ranges from about 60 seconds to about 150 seconds.

52. The method of claim 24 wherein:
(a) the assay droplet is incubated for a time that is less than about 240 seconds;
(b) the droplet-based wash protocol is completed in a time that is less than about 300 seconds; and
(c) the detecting is completed in a time that ranges from about 30 seconds to about 180 seconds.

53. The method of claim 24 wherein:
(a) the assay droplet is incubated for a time that ranges from about 30 seconds to about 180 seconds;
(b) the droplet-based wash protocol is completed in a time that ranges from about 30 seconds to about 240 seconds; and
(c) the detecting is completed in a time that ranges from about 60 seconds to about 180 seconds.

54. The method of claim 24 wherein:
(a) the assay droplet is incubated for a time that ranges from about 60 to about 150 seconds;
(b) the droplet-based wash protocol is completed in a time that ranges from about 30 seconds to about 180 seconds;
(c) the detecting is completed in a time that is less than about 180 seconds.

55. A method of assaying a cardiac marker in a biological sample from a subject, the method comprising:
(a) providing a droplet actuator;
(b) loading the biological sample and assay reagents on the droplet actuator;
(c) executing droplet operations to create sample droplets from the sample and reagent droplets from the reagents on the droplet actuator; and
(d) executing droplet operations using the sample droplets and reagent droplets to produce a detectable signal indicative of the quantity of the cardiac marker in the biological sample wherein droplets producing signals above a top-end of a standard curve are subjected to an auto-dilution sequence conducted using droplet operations to adjust the concentration of analytes to within a suitable range of detection.

* * * * *